US011535902B2

(12) United States Patent
Chait et al.

(10) Patent No.: US 11,535,902 B2
(45) Date of Patent: Dec. 27, 2022

(54) RNA SEPARATION AND RELATED TECHNIQUES FOR DETERMINING VIRUSES SUCH AS CORONAVIRUSES

(71) Applicant: Analiza, Inc., Bay Village, OH (US)

(72) Inventors: Arnon Chait, Bay Village, OH (US); Boris Y. Zaslavsky, Solon, OH (US)

(73) Assignee: Analiza, Inc., Bay Village, OH (US)

( * ) Notice: Subject to any disclaimer, the term of this patent is extended or adjusted under 35 U.S.C. 154(b) by 0 days.

(21) Appl. No.: 17/695,994

(22) Filed: Mar. 16, 2022

(65) Prior Publication Data

US 2022/0298589 A1    Sep. 22, 2022

Related U.S. Application Data

(60) Provisional application No. 63/162,485, filed on Mar. 17, 2021.

(51) Int. Cl.

| | |
|---|---|
| *C12N 15/10* | (2006.01) |
| *C12N 9/22* | (2006.01) |
| *C12N 15/11* | (2006.01) |
| *C12N 15/63* | (2006.01) |
| *C12Q 1/6816* | (2018.01) |
| *C12Q 1/70* | (2006.01) |
| *A61K 9/51* | (2006.01) |
| *A61K 39/215* | (2006.01) |
| *G01N 33/52* | (2006.01) |
| *G01N 33/569* | (2006.01) |

(52) U.S. Cl.
CPC ............... *C12Q 1/701* (2013.01); *A61K 9/51* (2013.01); *A61K 39/215* (2013.01); *G01N 33/523* (2013.01); *G01N 33/56983* (2013.01); *G01N 2333/165* (2013.01)

(58) Field of Classification Search
CPC ............ C12Q 1/6816; C12Q 2563/155; C12Q 2563/179; C12N 9/22; C12N 2310/20
See application file for complete search history.

(56) References Cited

U.S. PATENT DOCUMENTS

| 7,968,350 B2 | 6/2011 | Chait et al. | |
|---|---|---|---|
| 8,099,242 B2 | 1/2012 | Chait et al. | |
| 2014/0065642 A1* | 3/2014 | Chait | G01N 33/57434 |
| | | | 435/7.92 |
| 2015/0219655 A1 | 8/2015 | Chait et al. | |
| 2021/0364517 A1 | 11/2021 | Rotkin et al. | |

FOREIGN PATENT DOCUMENTS

| WO | WO 2004/111655 A1 | 12/2004 | |
|---|---|---|---|
| WO | WO 2019/144966 A1 | 8/2019 | |
| WO | WO2019144966 | * | 8/2019 |
| WO | WO 2021/173915 A1 | 9/2021 | |
| WO | WO 2021/185336 A1 | 9/2021 | |

OTHER PUBLICATIONS

PCT/US2021/019795, Jun. 18, 2021, Invitation to Pay Additional Fees.
PCT/US2021/019795, Aug. 11, 2021, International Search Report and Written Opinion.
Invitation to Pay Additional Fees dated Jun. 18, 2021, for International Application No. PCT/US2021/019795.
International Search Report and Written Opinion dated Aug. 11, 2021, for International Application No. PCT/US2021/019795.
International Preliminary Report on Patentability dated Sep. 9, 2022, for International Application No. PCT/US2021/019795.
International Search Report and Written Opinion dated Jul. 5, 2022, for International Application No. PCT/US2022/020484.
Cheung et al., A one-pot, isothermal DNA sample preparation and amplification platform utilizing aqueous two-phase systems. Anal Bioanal Chem. Aug. 2018:410(21):5255-5263. doi: 10.1007/00216-018-1178-4. Epub Jun. 8, 2018.
Iqbal et al., Aqueous two-phase system (ATPS): an overview and advances in its applications. Biol Proced Online. Oct. 28, 2016;18:18.
Jue et al., Using an aqueous two-phase polymer-salt system to rapidly concentrate viruses for improving the detection limit of the lateral-flow immunoassay. Biotechnol Bioeng. Dec. 2014; 111(12):2499-507. doi: 10.1002/bit.25316. Epub Aug. 25, 2014.
Paz et al., A simplified SARS-CoV-2 detection protocol for research laboratories. PLoS One. Dec. 18, 2020;15(12):e0244271.
U.S. Appl. No. 17/800,296, filed Aug. 17, 2022, Chait et al.
PCT/US2021/019795, Sep. 9, 2022, International Preliminary Report on Patentability.
PCT/US2022/020484, Jul. 5, 2022, International Search Report and Written Opinion.

* cited by examiner

*Primary Examiner* — Barry A Chestnut
(74) *Attorney, Agent, or Firm* — Wolf, Greenfield & Sacks, P.C.

(57) ABSTRACT

Certain aspects of the present disclosure generally relate to systems and methods for determining viruses such as coronaviruses. For instance, some aspects are directed to systems and methods for determining viruses using a partitioning system. Within the partitioning system, free RNA or other nucleic acids may preferentially partition into one phase, while intact viruses may be present in the other phase or in both phases. Accordingly, in some cases, free RNA or other nucleic acids may be preferentially removed, e.g., as compared to intact RNA or other nucleic acids present within a virus. In some cases, the phase containing intact viruses can be determined to determine the infectiousness, e.g., of a sample arising from a subject. This may be useful, for example, for distinguishing subjects who are capable of spreading an infection from those who are not infectious.

28 Claims, 3 Drawing Sheets

RNA SEPARATION AND RELATED TECHNIQUES FOR DETERMINING VIRUSES SUCH AS CORONAVIRUSES

RELATED APPLICATIONS

This application claims the benefit of U.S. Provisional Patent Application Ser. No. 63/162,485, filed Mar. 17, 2021, entitled "RNA Separation and Related Techniques for Determining Viruses such as Coronaviruses," by Chait, et al., incorporated herein by reference in its entirety.

FIELD

Certain aspects of the present disclosure generally relate to systems and methods for determining viruses such as coronaviruses.

BACKGROUND

Coronaviruses are a group of viruses that cause diseases in mammals and birds. In humans, coronaviruses cause respiratory tract infections that are typically mild, such as the common cold, though rarer forms such as SARS, MERS and COVID-19 can be lethal.

Coronaviruses are enveloped viruses with a positive-sense single-stranded RNA genome and a nucleocapsid of helical symmetry. The genome size of coronaviruses ranges from approximately 27 to 34 kilobases. The name coronavirus is derived from the Latin corona, meaning "crown" or "halo," which refers to the characteristic appearance of the virus particles: they have a fringe reminiscent of a crown or of a solar corona.

SUMMARY

Certain aspects of the present disclosure generally relate to systems and methods for determining viruses such as coronaviruses. The subject matter of the present disclosure involves, in some cases, interrelated products, alternative solutions to a particular problem, and/or a plurality of different uses of one or more systems and/or articles.

In one set of embodiments, the method comprises partitioning a biological fluid comprising a virus and free nucleic acid in an aqueous multi-phase partitioning system, and determining the virus within the partitioning system. In some cases, at least 95% of the free nucleic acid partitions in a first phase of the partitioning system.

The method, in another set of embodiments, comprises partitioning a biological fluid comprising a virus and free nucleic acid in an aqueous multi-phase partitioning system, removing an aliquot of the first phase, and sequencing the free nucleic acid within the aliquot. In some cases, at least 95% of the free nucleic acid partitions in a first phase of the partitioning system.

In another aspect, the present disclosure encompasses methods of making one or more of the embodiments described herein. In still another aspect, the present disclosure encompasses methods of using one or more of the embodiments described herein.

Other advantages and novel features of the present disclosure will become apparent from the following detailed description of various non-limiting embodiments of the disclosure when considered in conjunction with the accompanying figures.

BRIEF DESCRIPTION OF THE DRAWINGS

Non-limiting embodiments of the present disclosure will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the disclosure shown where illustration is not necessary to allow those of ordinary skill in the art to understand the disclosure. In the figures.

DETAILED DESCRIPTION

Figure 1:
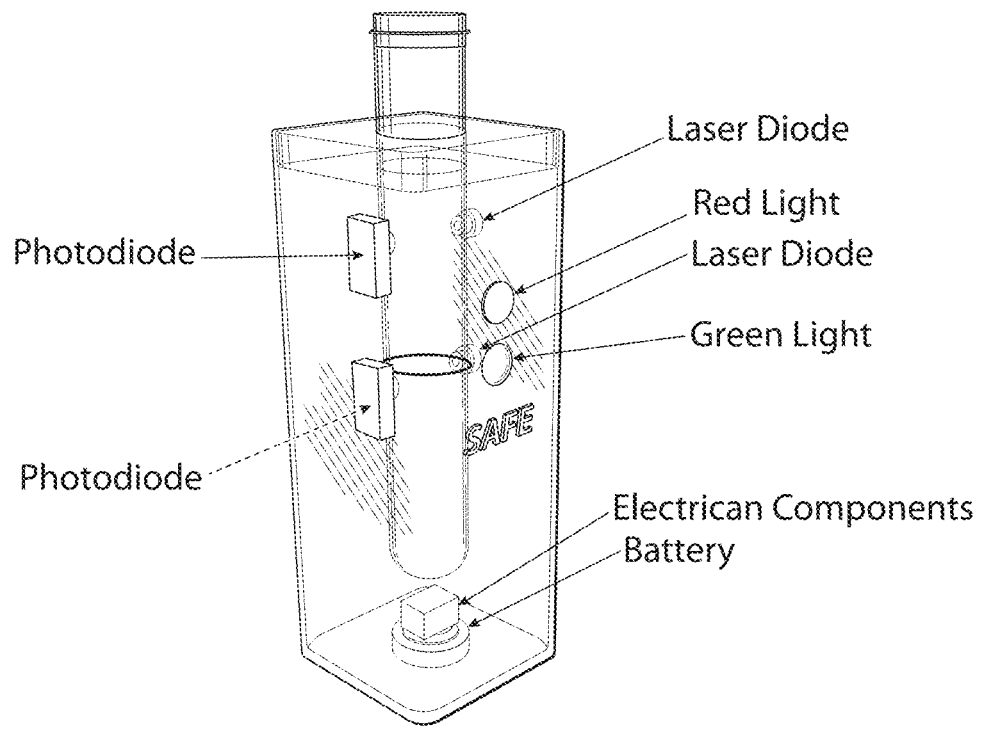
FIG. 1 illustrates an example device for determining a virus, in accordance with certain embodiments.

Certain aspects of the present disclosure generally relate to systems and methods for determining viruses such as coronaviruses. For instance, some aspects are directed to systems and methods for determining viruses using a partitioning system. Within the partitioning system, free RNA or other nucleic acids may preferentially partition into one phase, while intact viruses may be present in the other phase or in both phases. Accordingly, in some cases, free RNA or other nucleic acids may be preferentially removed, e.g., as compared to intact RNA or other nucleic acids present within a virus. In some cases, the phase containing intact viruses can be determined to determine the infectiousness, e.g., of a sample arising from a subject. This may be useful, for example, for distinguishing subjects who are capable of spreading an infection from those who are not infectious.

One aspect of the present disclosure is concerned with the detection of whole virus particles in biological samples containing a mixture of said whole virus particles, other virus components such as RNA (or other nucleic acids) that are recognized by a molecular detection system, e.g., RT-PCR, as belonging to the virus, and other biological or non-biological components that are not recognized by a molecular detection system as belonging to said virus. Some embodiments include techniques for distinguishing positive molecular detection of a whole virus particle and viral components using the same molecular detection system. This may provide for the determination of samples capable of further infection from those that are not, which may, e.g., be useful for clinically separating patients who are capable of spreading an infection from those who are sick but otherwise non-infectious.

Certain embodiments rely on spatial separation of whole virus particles from other components of the same virus, e.g., RNA. While whole virus particles may be partitioned between aqueous phases of a partitioning system such as an aqueous multi-phase partitioning system, free nucleic acids such as RNA (e.g., not contained within a virus) can be partitioned preferentially to one phase, e.g., predominantly due to their net negative electrical charge. The aqueous multi-phase partitioning system can include two or more phases, e.g., as is discussed herein. In some cases, if a sample contains both free RNA from dead viruses and whole functional virions capable of further infection, that sample could be detected by simple molecular testing of the phase in which free RNA is not substantially present. If RNA is found in that phase, it may help to determine the presence of whole, functional virions in the sample.

In some embodiments, there may be no need to determine or make otherwise quantitative use of a partition coefficient of an aqueous multi-phase partitioning system. For instance, the partitioning system itself may be able to separate free RNA (e.g., released from dead or damaged viruses) from whole functional virus particles, for example, by preferentially partitioning free RNA into one phase of the partitioning system. Other phases which are substantially free of RNA can then be analyzed, e.g., to determine the presence of virus particles. Of course, it should be understood that in other embodiments, the partition coefficient of free RNA and/or virus particles may be determined, e.g., as is described herein.

In one set of embodiments, whole viruses may be distributed to both phases. However, in other embodiments, whole viruses may be selectively or preferentially partitioned, e.g., to one of the phases of the partitioning system. For instance, at least 20%, at least 30%, at least 40%, or at least 50% of the viruses may be found in each phase of the partitioning system. In addition, in some embodiments, free RNA (or other nucleic acids) may be preferentially partitioned to one of the phases of the partitioning system. For example, at least 50%, at least 55%, at least 60%, at least 65%, at least 70%, at least 75%, at least 80%, at least 85%, at least 90%, at least 95%, at least 99%, etc. of the free RNA (or other nucleic acids) of the free nucleic acid molecules within the partitioning system may be present in one phase.

In certain embodiments, an assay of one (or more) of the phases of the partitioning system may be used to determine the presence of nucleic acids. Examples of such assays include, but are not limited to, RT/PCR or other sequencing techniques known to those of ordinary skill in the art. Sequencing and other assay techniques that can be used include any of those described herein. In some embodiments, aliquots of the phases of the partitioning system may be removed for analysis, although in other embodiments, the phases may be determined within the partitioning system itself, in situ, i.e., without necessarily removing aliquots of the phases of the partitioning system and using them for analysis.

In some aspects of the present disclosure, systems and methods for determining viruses are described. Examples of viruses that can be determined include, but are not limited to, coronaviruses, influenza viruses, or other viruses such as those described herein. In one set of embodiments, a partitioning system, such as an aqueous multi-phase partitioning system, is used. A sample, e.g., of a biological fluid taken from a subject, may be analyzed to determine whether a species of virus is present (e.g., SARS, MERS, COVID-19, etc.), and/or a type of virus is present (e.g., a coronavirus). The biological fluid may also be collected from a subject. Biological fluids may, in some cases, be processed for further use. Specific viruses, in certain embodiments, can be determined in the biological fluid. Further non-limiting examples of viruses are described below. In addition, in some cases, different types of viruses may be distinguished from each other (e.g., a coronavirus versus an influenza virus).

The sample of biological fluid may comprise fluids such as whole blood, blood serum, blood plasma, saliva, nasal fluid, sputum, urine, CNS fluid, breast nipple aspirate fluid, cerebral spinal fluid, semen, or the like. The subject that the biological fluid is taken from may be human, or non-human, e.g., a non-human mammal. Non-human mammals include, but are not limited to, a dog, cat, horse, cow, pig, sheep, goat, chicken, primate, rat, and mouse. In some cases, the subject is one that is suspected of being infected with a virus. For example, the subject may have previously been exposed to someone having the virus, or may at least be suspected of potentially having the virus. In addition, in certain embodiments, the subject may not be suspected of potentially having a virus (e.g., the fluid may be collected during routine screening).

A variety of different viruses may be determined, in accordance with various embodiments. Non-limiting examples of viruses, including infectious viruses, include coronaviruses or influenza viruses. Other non-limiting examples include adenoviruses, coxsackieviruses, Epstein-Barr viruses, hepatitis viruses (A, B, and C), herpes simplex viruses (types 1 and 2), cytomegaloviruses, herpes viruses (type 8), HIV, measles viruses, mumps viruses, papilloma viruses, parainfluenza viruses, polioviruses, rabies viruses, respiratory syncytial viruses, rubella viruses, varicella-zoster viruses, etc.

In some embodiments, a coronavirus may be determined. Examples of coronaviruses include, but are not limited to, HCoV-229E, HCoV-0C43, SARS-CoV, HCoV-NL63, HKU1, MERS-CoV, or SARS-CoV-2. As discussed herein, in some cases, one or more proteins of the coronavirus may be used to determine the virus, e.g., by interaction with a binding moiety that is able to bind to the proteins, or a targeting species, such as are discussed herein. Examples of such proteins on viruses include, but are not limited to, peplomers, envelope proteins, membrane proteins, nucleocapsids, spike glycoproteins, hemagglutinin-esterase dimers (HE), or the like. In addition, in some cases, the nuclear material of the virus (for example, RNA) may be determined, e.g., by interaction with a binding moiety or a targeting species, etc.

In some embodiments, an influenza virus may be determined. Influenza viruses include genera such as Influenza virus A, Influenza virus B, Influenza virus C, Influenza virus D, Isavirus, Thogotovirus, and Quaranjavirus. Examples of influenza A viruses include, but are not limited to, H1N1, H1N2, H2N2, H3N1, H3N2, H3N8, H5N1, H5N2, H5N3, H5N8, H5N9, H7N1, H7N2, H7N3, H7N4, H7N7, H7N9, H9N2, H10N7, etc. Examples of Influenza B viruses include, but are not limited to, Victoria and Yamagata. In some cases, one or more proteins of the influenza virus may be used to determine the virus, e.g., by interaction with a binding moiety or a targeting species, such as are discussed herein. Non-limiting examples of such virial proteins include hemagglutinin, neuraminidase, membrane proteins, glycoproteins, nucleocapsids, etc. In addition, in some cases, the nuclear material of the virus (for example, RNA) may be determined, e.g., by interaction with a virus-binding moiety or a targeting species.

In one set of embodiments, the biological fluid is partitioned in a partitioning system, such as a two-phase partitioning system, or other multi-phase system, e.g., having 3 or more phases. Two, three, four, or more phases may be present in the multi-phase partitioning system. In some embodiments, the partitioning system is aqueous, e.g., where each of the fluids is aqueous. Such aqueous partition systems may include aqueous phases formed with water and different types of polymers, such as Dextran and PEG or Dextran and Ficoll®, by the same types of polymers with different molecular weights, such as Dextran-70 and PEG-600 or Dextran-70 and PEG-8,000, by the same polymers but containing different in type and/or concentration salt additives, different buffers of different pH and concentration, etc. Further examples of partitioning systems are described in more detail herein. However, it should be understood that in other embodiments, other types of multi-phase systems, e.g., containing non-aqueous phases, may be used.

In one aspect, partitioning systems such as those discussed herein may be used to partition free nucleic acids, e.g., arising from dead or damaged virion particles, that may be present in a sample. For instance, a partitioning system may be used to separate or concentrate free nucleic acids such as DNA or RNA, e.g., within one of the phases of the partitioning system. Partitioning systems that may be used include any of those described herein. In addition, in some cases, the amount or concentration of free nucleic acids in a sample may be determined, and optionally compared to RNA (or other nucleic acids) present within intact viruses. The type, amount, and/or concentration of RNA (or other nucleic acids) within one or more phases may be determined using any suitable technique, such as via polymerase chain reaction (PCR), sequencing and/or other assay techniques including those described herein, etc. As a non-limiting example, as discussed herein, intact viruses may partition in more than one phase, while RNA (or other nucleic acids) that are not present within intact viruses may preferentially partition to a single phase.

Intact viruses (e.g., virion particles) within one or more phases of the partitioning system may be determined using any suitable technique, including those discussed herein. The techniques for determining intact viruses and free nucleic acids may be the same or different. For instance, nucleic acids (e.g., RNA and/or DNA) may be extracted from the viruses, e.g., after separation, and determined in some fashion, e.g., via polymerase chain reaction (PCR), sequencing techniques including those described herein, or the like.

As a non-limiting example, if the partitioning behavior of free nucleic acid (e.g., arising from the virus) in the partitioning system is known, then the partitioning behavior of the nucleic acid may be compared to the partitioning behavior of a control, such as the free nucleic acid. This comparison may be used to determine the nucleic acid contained within intact viruses within the sample. For instance, a sample may be partitioned within a partitioning system, and one or more phases of the partitioning system may be removed or separated, e.g., for analysis using techniques such as those described herein. The one or more phases may be removed prior to determining the virus, or may be removed after determining the virus. After removal or separation, intact viruses within a phase may be processed to extract their nucleic acids, e.g., into solution. The amount and/or concentration of nucleic acids in the phases of the partitioning system may then be determined, and in some cases, used to determine a partition coefficient. The partition coefficient can, in some cases, be compared to the expected values for only free nucleic acid in the partition system, and any differences may be used to determine the existence of intact viruses within the sample, in addition to free nucleic acid, and e.g., an amount or concentration. In addition, in some embodiments, a single phase of a partitioning system such as is described herein may be determined, e.g., without necessary determining other phases or calculating a partition coefficient. For example, free RNA (or other nucleic acids) may preferentially partition into one phase of a partition system such as described herein, while other phases of the partitioning system may be determined, e.g., to determine its RNA content, which may be indicative of intact viruses. However, it should be understood that determining a partition coefficient is not required, and in some embodiments, no partition coefficient may be determined, for example, since only a single phase of the partitioning system is analyzed.

In certain embodiments, techniques such as those described herein can allow for the determination of intact viruses in a sample. In some cases, this may be related to the severity of the disease, the stage of illness, the infectiousness of the subject, or the like. In contrast, in many other techniques, it is not possible to distinguish intact viruses from viruses that have released their nucleic acids, e.g., into the sample.

As a non-limiting example, in one embodiment, a sample may be partitioned within the phases of a suitable partitioning system, e.g., such as has been described herein. After equilibration, aliquots of one or more of the phases may be taken, and optionally one or more of them may be processed in some fashion, e.g., to cause any intact viruses that might be present to release their nucleic acids into solution. However, in some cases, the virus may be determined within the partitioning system itself, in situ, i.e., without necessarily removing aliquots of one or more of the phases from the partitioning system to be analyzed. The nucleic acids in one (or more) of the phases may be determined, e.g., using PCR or other sequencing techniques such as those described herein. In some cases, the amount of a particular nucleic acid sequence (e.g., the RNA of the virus) may be determined in one or more of the phases, and used to determine the presence of intact viruses within the sample, e.g., by eliminating or reducing free nucleic acids (such as RNA or DNA) caused by dead or damaged viruses. This may be particularly useful if the partitioning system is chosen to be selectively preferential to free nucleic acids, e.g., such that at least 50%, at least 55%, at least 60%, at least 65%, at least 70%, at least 75%, at least 80%, at least 85%, at least 90%, at least 95%, at least 99%, etc. of free nucleic acid is present in one phase, for instance, as is discussed herein. In some embodiments, the differences can be quantified and used to determine the relative amount or concentration of intact virus present within the sample.

In certain embodiments, a partitioning system causes the sample to partition such that intact viruses (e.g. SARS-CoV-2 virions, or other viruses such as those described herein) appear in both phases. In certain embodiments, the partitioning system can also cause the sample to partition such that nucleic acids or antigens arising from non-intact viruses only or substantially appear in one (e.g. top or bottom) phase. One or more phases may then be determined, e.g., to determine the presence of nucleic acids or antigens (e.g. spike protein antigens) arising from the virus, e.g. using PCR techniques such as RT/PCR to determine the presence of nucleic acids, or using antigen tests to determine the presence of antigens.

Such systems can be used, for example, to distinguish between positive cases only (e.g., as determined by the presence of RNA or other free nucleic acids) and positive infective cases (e.g., as determining using free nucleic acids plus intact viruses). This can be achieved, for example, since one phase may contain nucleic acids arising from intact viruses, while another phase may also contain free RNA, or other nucleic acids (e.g., DNA). For instance, the partitioning system may be structured such that highly charged species, such as free nucleic acids, are preferentially partitioned in one phase. For instance, at least 50%, at least 55%, at least 60%, at least 65%, at least 70%, at least 75%, at least 80%, at least 85%, at least 90%, at least 95%, at least 99%, etc. of the free nucleic acid molecules within the partitioning system may be present in one phase. Thus, in certain embodiments, for example, determining an intact virus within a first phase and a nucleic acid or antigen arising from the virus in a second phase may advantageously indicate positivity and infectiousness, etc.

As previously discussed, aqueous partitioning systems with two or more phases may be used in various aspects of the disclosure to determine one or more viruses (or other species). For instance, as discussed herein, one or more viruses may be determined within an aqueous two-phase partitioning system, e.g., by determining the amount and/or concentration of the viruses in each of the phases using techniques such as those described herein, while partitioning free RNA or other nucleic acids predominately into one of the phases, e.g., due to their net negative electrical charge. In general, the properties of aqueous two-phase partitioning systems that contribute to solute partitioning include parameters as described in greater detail below. However, since nucleic acids such as RNA are generally (negative) charged molecules, one parameter that influences its partitioning behavior between the two phases is the difference in the ionic composition of the phases in the partitioning system, e.g., via salt as an additive and its distribution.

Aqueous multi-phase systems are well-known to those of ordinary skill in the art, and can arise in aqueous mixtures of different water-soluble polymers or a single polymer and a specific salt. When two or more certain polymers, e.g., dextran ("Dex") and polyethylene glycol ("PEG"), or one or more certain polymers and one or more inorganic salts, e.g. polyvinylpyrrolidone ("PVP") and sodium sulfate, are mixed in water above certain concentrations, the mixture can separate into two (or more) immiscible aqueous phases under certain conditions. There may be, in certain instances, a discrete interfacial boundary separating any two phases, for example, such that one is rich in one polymer and the other phase is rich in the other polymer or the inorganic salt. The aqueous solvent in one or more phases may provide a medium suitable for biological products. Two-phase systems can also be generalized to multiple phase system by using different chemical components, and aqueous systems with a dozen or more phases are known in the art.

When a species, such as a virus, is introduced into such a two-phase system, it may distribute between the two phases, and this understanding can be extended to three or more phases. In this and other systems, the species can be found at different concentrations within each phase, or can be at the same concentration within each phase. Partitioning of a solute can be characterized by the partition coefficient "K," defined as the ratio between the concentrations of the solute the two immiscible phases at equilibrium. It has previously been shown that phase separation in aqueous polymer systems may result from different effects of two polymers (or a single polymer and a salt) on the water structure (B. Zavlavsky, *Aqueous Two-Phase Partitioning: Physical Chemistry and Bioanalytical Applications*, Marcel Dekker, New York, 1995). As the result of the different effects on water structure, the solvent features of aqueous media in the coexisting phases can differ from one another. The difference between phases may be demonstrated by techniques such as dielectric, solvatochromic, potentiometric, and/or partition measurements.

The basic rules of solute partitioning in aqueous two-phase systems have been shown to be similar to those in water-organic solvent systems (which can also be used as systems in the present disclosure). However, what differences do exist in the properties of the two phases in aqueous polymer systems are often very small, relative to those observed in water-organic solvent systems, as would be expected for a pair of solvents of the same (aqueous) nature. The small differences between the solvent features of the phases in aqueous two-phase or multi-phase systems can be modified so as to amplify the observed partitioning that results when certain structural features are present.

It is known that the polymer and salt compositions of each of the phases usually depend upon the total polymer and/or salt composition of an aqueous two-phase system. The polymer and/or salt composition of a given phase, in turn, usually governs the solvent features of the aqueous media in this phase. These features include, but are not limited to, dielectric properties, solvent polarity, ability of the solvent to participate in hydrophobic hydration interactions with a solute, ability of the solvent to participate in electrostatic interactions with a solute, and hydrogen bond acidity and basicity of the solvent. All these and other solvent features of aqueous media in the coexisting phases may be manipulated by selection of polymer and salt composition of an aqueous two-phase system. These solvent features of the media may govern the sensitivity of a given aqueous two-phase system toward a particular type of solvent accessible chemical groups in the receptor. This sensitivity, type, and topography of the solvent accessible groups in two different proteins, for example, can determine the possibility of separating proteins in a given aqueous two-phase system.

In some cases, a particularly sensitive system may be required, i.e., a system that is very sensitive to, and able to determine a partition coefficient or a relative measure of interaction with respect to, two very similar species. This sensitivity may be of importance when, for example, subtle differences are being detected between the conformational changes in a receptor induced by binding of closely related chemical compounds. The present disclosure provides, in one set of embodiments, efficient and successful systems and methods for screening aqueous phase compositions to identify and/or amplify differences between the compositions of two mixtures. By utilizing a wide variety of different conditions to screen each molecule, as described herein, different partitioning behavior may be obtained reliably without the need to fully understand the underlying theory of aqueous two-phase partitioning, or any of the other related or substitutable techniques.

Viruses may be distributed between the two or more phases when placed into such a system. For example, in the case where phase-forming polymers are used, solutions comprising one or more of the two polymers and a virus may be mixed together such that both phase-forming polymers and the virus are mixed. The resulting solution is resolved and a two-phase system is formed. Optionally, centrifugation can be used to enhance separation of the phases. It will be recognized by those of ordinary skill in the art that partitioning behavior of a virus may be influenced by many variables, such as the pH, the polymers used, the salts used, factors relating to the composition of the system, as well as other factors such as temperature, volume, etc. Optimization of these factors for desired effects can be accomplished by routine practice by those of ordinary skill in the relevant arts, in combination with the current disclosure. In addition, as previously discussed, the partitioning behavior of a virus may be altered, for example, using a targeting species able to bind to the virus, e.g., selectively.

In contrast, in some embodiments, RNA, DNA, or other nucleic acids that are not contained within a virus particle may predominantly partition into one or a limited number of phases. As discussed herein, this may be caused, for example, due to the relatively high net negative electrical charge of nucleic acids, e.g., as compared to virus particles.

Accordingly, in some embodiments, such free nucleic acids may be predominantly found in one or a limited number of phases, while virus particles may be present in other phases. By analyzing the phases that do not have the free nucleic acids, the virus particles can be determined, e.g., as discussed herein.

Evaluation of data from partitioning of a virus can involve use of the partition coefficient, in some embodiments of the disclosure. However, it should be understood that partition coefficients are not always required. For example, the partition coefficient of a virus can be taken as the ratio of the virus in first phase to that in the second phase in a biphasic system. When multiple phase systems are formed, there can be multiple independent partition coefficients, each of which can be defined between any two phases. It will be recognized that the partition coefficient for a given virus may be constant if the conditions and the composition of the two-phase system to which it is subjected remain constant. Thus, if changes are observed in the partition coefficient for a virus upon addition of a potential binding partner (for example, an antibody), these changes can be presumed to result from changes in the virus structure caused by formation of a complex with the virus. The partition coefficient K, as used herein, is a specifically mathematically defined quantity as further described herein, and the term includes coefficients representing the relative measure of interaction between a species, such as a virus, and at least two interacting components. It should also be recognized that differences between partition coefficients of different species in two or more mixtures could indicate, in addition to potential structural changes, also binding or lack of binding of such species to other species in the mixtures.

In a non-limiting example of one partitioning system, aqueous multi-phase systems are known to be formable from a variety of substances. For example, in order to determine the partition coefficient of a virus (or a mixture of viruses) to be analyzed, concentrated stock solutions of all the components (polymer 1, e.g., dextran; polymer 2, e.g., PEG, polyvinylpyrrolidone, salts, etc.) in water can be prepared separately. The stock solutions of phase polymers, salts, etc. can be mixed in the amounts and conditions (e.g., pH from about 3.0 to about 9.0, temperature from about 4° C. to 60° C., salt concentration from 0.001 to 5 mol/kg) appropriate to bring the system to the desired composition and vigorously shaken. The system can then be allowed to equilibrate (resolve the phases). Equilibration can be accomplished by allowing the solution to remain undisturbed, or it can be accelerated by centrifugation, e.g., for 2-30 minutes at about 1000 g to 4000 g, or higher. Aliquots of each settled (resolved) phase can be withdrawn from the upper and/or lower phases (or from one or more phases, if multiple phases are present). The concentration of viruses within the phases can be determined for one or more of the phases.

Different assay methods may be used to determine species within the phases of a partitioning system, such as those described herein. Such assays may be used, for instance, to determine the concentration of the viruses in each phase of a multi-phase system. The assays will often depend upon the identity and type of viruses or other viruses present. Examples of suitable assay techniques include, but are not limited to, spectroscopic, immunochemical, chemical, fluorescent, radiological and enzymatic assays. In some cases, a virus may be determined by determining a peptide or protein associated with the virus. Non-limiting examples, include peplomers, envelope proteins, membrane proteins, nucleocapsids, etc. of coronaviruses, or hemagglutinin or neuraminidase of influenza viruses. Such peptides or proteins may be determined, for example, using suitable antibodies able to interact with these. For example, certain immunochemical assays can be used in some cases, e.g., ELISA. In addition, other peptide or protein detection techniques can be used in certain embodiments. These include, but are not limited to, direct spectrophotometry (e.g., monitoring the absorbance at 280 nanometers) and dye binding reactions with Coomassie Blue G-250 or fluorescamine, o-phthaldialdehyde, or other dyes and/or reagents. Free nucleic acids may also be determined using sequencing and other techniques such as those described herein.

In some embodiments, one or more of the fluid manipulations may occur within a microfluidics device. "Microfluidic," as used herein, refers to a device, article, or system including at least one fluid channel having a cross-sectional dimension of less than about 1 mm. The "cross-sectional dimension" of the channel is measured perpendicular to the direction of net fluid flow within the channel. Thus, for example, some or all of the fluid channels in an article can have a maximum cross-sectional dimension less than about 2 mm, and in certain cases, less than about 1 mm. In one set of embodiments, all fluid channels in an article are microfluidic and/or have a largest cross sectional dimension of no more than about 2 mm or about 1 mm. In certain embodiments, the fluid channels may be formed in part by a single component (e.g. an etched substrate or molded unit). Of course, larger channels, tubes, chambers, reservoirs, etc. can be used to manipulate in other embodiments of the disclosure. In one set of embodiments, the maximum cross-sectional dimension of the channels in an article is less than about 1 mm, less than about 500 micrometers, less than about 300 micrometers, less than about 200 micrometers, less than about 100 micrometers, less than about 75 micrometers, less than about 50 micrometers, less than about 30 micrometers, less than about 25 micrometers, less than about 20 micrometers, less than about 15 micrometers, less than about 10 micrometers, less than about 5 micrometers, less than about 3 micrometers, less than about 2 micrometers, less than about 1 micrometer, less than about 500 nm, less than about 300 nm, less than about 100 nm, or less than about 50 nm. In some cases, suitable microfluidics devices may be readily obtained commercially.

As mentioned above, certain aspects of the present disclosure are generally directed to the investigation of the state of a virus, although the disclosure is not limited to only viruses. Other embodiments can be applied to essentially any molecular species and/or interaction, whether biological, biochemical, chemical, or other species, and those of ordinary skill in the art will understand how the disclosure can be used in the context of other molecules. Accordingly, it is to be understood that whenever "virus" is used in the description herein, any other biological or non-biological molecule also can be used or studied in other embodiments.

Some embodiments are directed to techniques for determining information about compositions suspected of containing viruses, and/or molecules able to interact with viruses. The composition may originate from a biological fluid (or other sample), such as a human clinical sample or other biological fluid, tissue, cells, a subject, etc., or the mixture may be a synthetic mixture. The mixture can come from a biological system (e.g., a subject) which includes, but is not limited to, a human or non-human mammal. Non-human mammals include, but are not limited to, a dog, cat, horse, cow, pig, sheep, goat, chicken, primate, rat, and mouse.

Some embodiments are related to developing and determining characteristics (quantitative and/or qualitative) of a mixture that are obtained, for example, via processing using multi-phase partitioning, which can reflect certain structural and functional characteristics of viruses that may be present within the sample. These characteristics can be used, for example, for establishing relationships between the composition of the sample and the physiological state of the biological source of the sample, e.g., the state of health or disease of a subject, such as a human subject. These characteristics can also be used to design experimental conditions for subsequent fractionation of the mixtures into subsets enriched in the molecule(s) of interest for the purpose of the analysis, while simultaneously reduced in the total number of different molecule(s) in some cases. Certain systems and methods can also be useful for detecting, classifying, and/or predicting changes in samples containing viruses. For example, the sample may be one associated with a particular disease or physiological state of a living organism, cells, tissues, or biological liquids. Certain systems and methods can also be used to detect changes to viruses in a biological sample and these changes could further be used to detect and classify a diagnostic that is related to such changes.

Examples of such changes in a mixture can be the differences in a property of a virus of the mixture, such as its conformation, structure and/or interaction tendency with respect to another molecule or molecules (e.g., its binding affinity or other interaction characteristic with respect to another molecule or molecules). For example, if the mixture includes viruses, such changes may be induced through primary sequence modification, by degradation of the virus through chemical, thermal, or other degradation mechanisms, by interaction with other molecules and/or biomolecules, by interaction with low molecular weight compounds (e.g., hormones, peptides, vitamins, cofactors, etc.), by changes in the relative content or concentration of the constituents of the mixture, by reactions such as enzymatic reactions, etc. Some systems and methods can be used, in certain cases, to detect, analyze and/or characterize biological materials as they interact with viruses, including but not limited to, polypeptides, proteins, carbohydrates, nucleic acids, polynucleotides, lipids, sterols, and mixtures or derivatives thereof, e.g., for the purpose of detection of, or onset of, a particular disease or physiological state, monitoring its progress, treatment, etc.

Comparison and classification steps involved in various embodiments of the disclosure can make use of additional information not necessarily related to (not directly derived from) the analytical methods of the disclosure. For example, blood pressure, temperature, blood glucose level, and/or essentially any other measurable physiological condition can be used in conjunction with various techniques of the disclosure to analyze one or more diseases or conditions.

It will be recognized by those of ordinary skill in the art that these biological materials can be found in any suitable form, for example, in the form of extracts from natural sources, biological liquids, collections of molecules generated by combinatorial chemical or biochemical techniques and combinations thereof, synthetically created, etc. In one set of embodiments, the biological materials arise from a biological fluid (e.g., withdrawn from a subject), and such biological materials may include one or more viruses suspected of being present within the subject, e.g., the subject may be suspected of being infected by one or more viruses. In some embodiments, the viruses may not be suspected of being present within the biological materials, e.g. during routine screening.

In one embodiment, the present disclosure provides a method to determine certain conditions under which variations among samples representing different species (e.g., viruses), or mixtures of species could be detected, i.e., determining a set of criteria and/or system components as a "tool," or a part of a tool, to determine information, as well as the subsequent use of the tool. For example, the ability of a system to determine a partition coefficient or a relative measure of interaction between a species, such as a virus, and one or more interacting components that can define one or more phases of the system can serve as an important tool or component of such a tool. Specifically, as one example, the partitioning of the constituents of a sample between two phases having different chemical or biochemical affinities or other characteristics, such as solvent structures, may separate the constituents by their relative affinity for media of different properties or composition. This separation technique thus can include or, alternatively, can be unlike those typically used in proteomics or similar techniques, e.g., 2-D gel electrophoresis, in which charge and size differences are the two dimensions used to separate the constituents of a sample. Some embodiments provide the ability for performing sequential or serial partitioning, with either the same of different conditions, which may result in additional amplification of differences in the fractionated samples. These fractions may be further analyzed using standard proteomics techniques.

As mentioned elsewhere herein, aqueous multi-phase (e.g., two-phase) partitioning systems are well-suited for use in many or most embodiments of the disclosure, but other partitioning systems can be used. Where terms such as "aqueous two-phase partitioning" or "aqueous multi-phase partitioning" is used, it is to be understood that other systems can be used in other embodiments, such as those described herein. Partitioning of a biopolymer in aqueous two-phase systems may depend on its three-dimensional structure, type and topography of chemical groups exposed to the solvent, etc. Changes in the 3-D structure of a receptor induced by some effect, e.g., by binding of a ligand binding or by structural degradation, also can change the topography of solvent accessible chemical groups in the biomolecule, or both the topography and the type of the groups accessible to solvent. One result of these changes may be an alteration in the partition behavior of the biomolecule or other species.

Viruses can be determined to diagnose or determine an underlying physiological condition or disease. Rapid and specific quantification techniques are readily available to those of ordinary skill in the art which can be used to quantify the concentration of viruses using standard methods and techniques directly in the biological sample, e.g., using antibodies in an Enzyme Linked ImmunoSorbent Assay (ELISA). The concentrations in the two interacting components of each system can be used to calculate the values of the partition coefficients. Changes to the individual values of the partition coefficients thus may indicate certain changes to the viruses. In some cases, the change to the partition coefficient of one or more viruses, can result in a definitive diagnosis of a disease or condition. In yet other cases, partitioning of the samples in multiple systems and performing the steps above, then observing the pattern of values for one or more viruses, can provide an alternative way to constructing a sensitive and specific diagnostics method.

Thus, for example, a sample may be obtained from a subject, and partitioned in one or more aqueous two-phase (or multi-phase) partitioning systems. Partition coefficients for one or more viruses may be determined, and used to determine a physiological condition of the subject, e.g., determining the presence and/or risk level of viruses in a subject. In some cases, the partition coefficients may be compared to reference partition coefficients, e.g., reference values previously determined for biomolecules taken from subjects with and without a disease or condition, e.g., viral infections.

For example, in connection with certain embodiments, a variety of studies can take place. For example, the studies may include determining analysis procedures that involve taking samples from a single subject or multiple subjects. For example, a subject may be suspected of being infected by a virus. For instance, in one embodiment, the type of virus may be determined as described herein. For example, a coronavirus may be distinguishable from an influenza or other type of virus.

Similarly, changes may be detected using other systems and methods which have an underlying dependence upon the topography and/or the types of solvent accessible groups. Examples of such other methods include, but are not limited to, column liquid-liquid partition chromatography (LLPC), a heterogeneous two-phase system, or a multi-phase heterogeneous system. In some cases, an apparent partition coefficient may be generated that expresses the relative changes in the average partitioning between a first and a second phase, e.g., of a virus. For example, in LLPC, the retention volume of a receptor may be used as the apparent partition coefficient.

In certain embodiments, the partitioning system may comprise an agent comprising a binding moiety, e.g., that is able to bind to a virus. Such agents may attach to target viruses within the sample via virus-binding moieties and/or a targeting species, e.g., by attaching to one or more proteins within the virus, for example, proteins such as peplomers, envelope proteins, membrane proteins, nucleocapsids, spike glycoproteins, hemagglutinin-esterase dimers (HE), or the like. For example, in some embodiments, a virus-binding moiety may bond to a protein (e.g. a peplomer) of a virus (e.g. a coronavirus such as COVID-19). In some cases, for example, the binding moiety may contain an antibody that is able to attach to the proteins.

In some cases, the agent may also comprise a particle, such as a nanoparticle. In some embodiments, at least some of the particles may be partially or fully coated with a virus-binding moiety, such as RNA or an antibody, or other virus-binding moieties such as those described herein. The agent may also comprise other moieties, such as signaling moieties and/or other moieties such as those described herein.

The binding moiety, in some cases, may also be attached to particles, such as gold or other nanoparticles, which may result in the formation of a complex of particles around a virus. As another example, the complex itself may contain a signaling moiety, e.g., attached to the particle, or the particle itself may contain a signaling moiety. In some cases, the complex itself may be detectable, e.g., as a change in color, even, in some embodiments, without a signaling moiety. Thus, for instance, if the signaling moiety is a dye, or is fluorescent, then the amount or concentration of signaling moiety in the phases of the partitioning system can be determined, for example, using fluorescence, absorbance, plate readers, or by visual inspection (i.e., visually). In some embodiments, the particles themselves are fluorescent. In addition, in some cases, more than one type of virus may be determined using such a system. For example, a binding moiety may be selective for a coronavirus but not an influenza virus, or vice versa, such that the binding moiety may substantially alter the partitioning behavior of one virus, or complexes including the virus, relative to the other. In such fashion, viruses may be readily distinguished from each other.

The virus-binding moiety may be selected to bind to a virus or at least a portion thereof, e.g., a protein of the virus, viral RNA, etc. In some cases, the binding may be specific. For example, the binding affinity of the virus-binding moiety to a portion of the virus may be less than 1 mM, less than 100 nM, less than 10 nM, or less than 1 nM. In some cases, the virus-binding moiety may bind to at least a portion of the virus to a significantly higher degree than to other molecules. For instance, the binding affinity may be at least 10×, 100×, or 1000× greater than for any other molecules that are present, e.g., in a sample of biological fluid. In some cases, the binding may be essentially irreversible, although it need not be in other cases. Thus, for example, in the case of a receptor/ligand binding pair the ligand would specifically and/or preferentially select its receptor from a complex mixture of molecules, or vice versa. An enzyme would specifically bind to its substrate, a nucleic acid would specifically bind to its complement, an antibody would specifically bind to its antigen, etc.

In some embodiments, one or more agents bind to a virus. For example, in some embodiments at least 1, at least 2, at least 4, at least 5, at least 10, at least 50, at least 100, at least 200, or more agents bind to a virus. In some embodiments, up to 500, up to 200, up to 100, up to 50, up to 10, up to 5, up to 4, or up to 2 agents bind to a virus. Combinations of these ranges are possible. For example, in some embodiments at least 1 and up to 500 agents may bind to a virus.

The binding interactions may be, for example, hydrogen bonds, van der Waals forces, hydrophobic interactions, covalent coupling, or the like. In addition, in some embodiments, the virus-binding moiety may be selected so as to selectively bind to a first virus, relative to a second virus. For example, the virus-binding moiety may be able to selectively bind a coronavirus relative to an influenza virus, or vice versa. Virus-binding moieties may comprise, for example, antibodies (e.g., able to bind to a protein, for example, the proteins described herein for coronaviruses, influenza viruses, etc.), or nucleic acids (e.g., able to bind to nucleic acids, such as RNA or DNA, arising from a virus, e.g., such that the virus-binding moiety comprises a nucleic acid sequence substantially complementary to a portion of the virus's genome). For example, the antibody may be an IgA. Other non-limiting examples include IgG, IgM, IgD and IgE.

In some cases, the antibody is a protein or glycoprotein consisting of one or more polypeptides substantially encoded by immunoglobulin genes or fragments of immunoglobulin genes. The recognized immunoglobulin genes include the kappa, lambda, alpha, gamma, delta, epsilon, and mu constant region genes, as well as myriad immunoglobulin variable region genes. Light chains may include kappa or lambda. Heavy chains may include gamma, mu, alpha, delta, or epsilon, which in turn include immunoglobulin classes such as IgG, IgM, IgA, IgD, or IgE. A typical immunoglobulin (antibody) structural unit may comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively. Antibodies exist as intact immunoglobulins or as a number of well-characterized fragments, e.g., which can be produced by digestion with various peptidases. Thus, for example, pepsin can digest an antibody below (i.e., toward the Fc domain) the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region thereby converting the (Fab')2 dimer into an Fab' monomer. The Fab' monomer is essentially a Fab with part of the hinge region. While various antibody fragments are defined in terms of the digestion of an intact antibody, such fragments may also be synthesized de novo, for example, chemically by utilizing recombinant DNA methodology, by "phage display" methods, or the like. Examples of antibodies include single chain antibodies, e.g., single chain Fv (scFv) antibodies in which a variable heavy and a variable light chain are joined together (directly or through a peptide linker) to form a continuous polypeptide.

The signaling moiety, if present, may be any entity that can be determined, e.g., to determine the partitioning of the virus. For instance, upon binding of the virus-binding moiety to the virus, the signaling moiety may be determined, qualitatively and/or quantitatively, in the partitioning system, e.g., to allow the partitioning of the virus within the partitioning system to be determined. The signaling moiety, may be for example, colored, fluorescent, radioactive, etc. Non-limiting examples of signaling moieties include a dye, a fluorescent dye, a chemiluminescent entity, a radioactive label, an isotope such as a non-radioactive isotope or an isotope detectable by mass spectrometry, a ligand which can serve as a specific binding partner to a labeled antibody, an enzyme, an antibody which can serve as a specific binding partner for a labeled ligand, an antigen, a group having a specific reactivity, and/or an electrochemically detectable moieties. Non-limiting examples of dyes or fluorescent signaling moieties include fluorescein, calcein, rhodamine, Green Fluorescent Protein (GFP), etc. Those of ordinary skill in the art will be aware of other fluorescent entities that are readily commercially available.

The signaling moiety may be determined, in some cases, using a suitable detector, although in certain embodiments, the signaling moiety can be determined unaided, e.g., to the naked eye. Examples of suitable detectors include, but are not limited to, microscopes (e.g., fluorescence microscopes), plate readers, ELISA readers, Geiger counters, mass spectrometers, cameras (e.g., within smart phones or cell phones) or the like. Other examples of detectors include any of those described herein. In some cases, the signaling moiety may be colorimetrically determined (e.g. within the phases of the partitioning system). The signaling moiety can also be determined, in some embodiments, by determining a color change in at least one phase of the partitioning system. The signaling moiety may also be determined fluorescently, in some embodiments. In some cases, the signaling moiety may be determined using ELISA (e.g. within the phases of the partitioning system).

Binding of the agent, in some cases, may also alter the partitioning of the virus. For example, the agent may bind to the virus via the virus-binding moiety, thereby altering the effective structure of the virus, and at least in some cases, its partitioning. Accordingly, upon binding of the virus-binding moiety to a virus, the partitioning of the agent may appear to change, which can be determined, for example, by determining a change in the partitioning of the signaling moiety within the partitioning system. In some cases, the change in partitioning may be relatively substantial. For example, the change in partitioning may be such that in the presence (or absence) of the virus, the agent partitions such that at least 50% (by number), at least 55%, at least 60%, at least 65%, at least 70%, at least 75%, at least 80%, at least 85%, at least 90%, at least 95%, etc. of the agent is in a single phase of the partitioning system.

In some cases, this change in partitioning may be intentional. For example, in certain embodiments, the agent may comprise other components whose partitioning behavior may change, e.g., upon binding to a virus.

A variety of methods may be used to determine partitioning of the virus in one or more phases within a partitioning system. For instance, in one set of embodiments, a signaling moiety may be determined, e.g., as discussed herein. In another set of embodiments, however, other methods may be used, for example, if no signaling moiety is present. For example, in one set of embodiments, aggregation of virus may be determined as a change in color or clarity, etc., within one or more phases of the partitioning system. A variety of systems may be used to determine the particles and/or the phases colorimetrically, for example, by determining the particles themselves, and/or signaling moieties or the like, e.g., as discussed herein. For example, the particle may be determined based on the partitioning of a signaling moiety within the phases of the partitioning system. As another example, the particle may be determined by exposing the agent to a second agent comprising a signaling moiety and a binding moiety able to bind to the agent and/or the virus. In some embodiments, the particle may be determined within phases of the partitioning system by determining a change in light scattering.

In some cases, partitioning of the virus in one or more phases within a partitioning system may be determined using a suitable detector, although in some embodiments, partitioning may be determined without a detector, e.g., by using the naked eye. Examples of suitable detectors include, but are not limited to, microscopes (e.g., fluorescence microscopes), plate readers, ELISA readers, Geiger counters, mass spectrometers, cameras (e.g., within smart phones or cell phones) or the like. Other examples include any of the detectors described herein. In some cases, the virus may be colorimetrically determined.

In some cases, the detector may be a handheld device or a portable device, such as the example shown in FIG. 1. As one example, a smart phone or a cell phone may be used to determine the signaling moiety. As another example, a cellphone or a smartphone can be used as a colorimetric detector. For example, an app or a program on a smartphone may be used to determine one, two, or more phases of the partitioning system, and if the colors or other characteristics of the phases meet certain criteria (e.g., different colors, different ratios of light scattering, different intensities, etc.), e.g., due to the formation of complexes in a phase, then the virus may be determined.

As yet another example, the agent may be determined by exposing the agent to a second agent comprising a signaling moiety and a binding moiety, where the binding moiety is able to bind the complex. For instance, the binding moiety may be able to bind to the virus, e.g., a virus-binding moiety, and/or bind to the particles. For example, in one set of embodiments, the second agent may comprise a signaling moiety and a virus-binding entity. The virus-binding entity of the second agent may be the same or different than the virus-binding entity of the agent, e.g., as described above.

As another example, the second agent may comprise a signaling moiety and a complex-binding entity, e.g., able to bind to the complex of the virus and the agent, as described above. For instance, the complex-binding entity may be selected to bind to the complex, e.g., specifically. For example, the binding affinity of the complex-binding moiety to a portion of the complex, such as to the particle, to the virus, etc. may be less than 1 mM, less than 100 nM, less than 10 nM, or less than 1 nM. In some cases, the complex-binding moiety may bind to a portion of the complex to a significantly higher degree than to other molecules, e.g., within the sample. For instance, the binding affinity may be at least 10×, 100×, or 1000× greater than for any other molecules or entities that are present. In some cases, the binding may be essentially irreversible, although it need not be in other cases. Thus, for example, in the case of a receptor/ligand binding pair the ligand would specifically and/or preferentially select its receptor from a complexed mixture of molecules, or vice versa. An enzyme would specifically bind to its substrate, a nucleic acid would specifically bind to its complement, an antibody would specifically bind to its antigen, etc. The binding interactions may be, for example, hydrogen bonds, van der Waals forces, hydrophobic interactions, covalent coupling, or the like. In addition, in some embodiments, the complex-binding entity may be selected so as to selectively bind to complexes of a first virus, relative to a second virus. For example, the complex-binding moiety may be able to selectively bind a coronavirus complex relative to an influenza virus complex, or vice versa. Exemplary complex-binding moieties may include or comprise, but are not limited to, antibodies (e.g., able to bind to a protein, for example, the proteins described herein for coronaviruses, influenza viruses, etc.), or nucleic acids (e.g., able to bind to nucleic acids, such as RNA or DNA, arising from a virus, e.g., such that the virus-binding moiety comprises a nucleic acid sequence substantially complementary to a portion of the virus's genome). For example, the antibody may be an IgA. Other examples include IgG, IgM, IgD and IgE.

In certain embodiments, a targeting species able to bind to a virus that may be present, e.g., in the partitioning system. The targeting species may be separate from the agent (e.g. the first agent and/or the second agent) in some embodiments. In certain embodiments, a virus may be exposed a targeting species within a partitioning system (e.g. a first aqueous multi-phase partitioning system, a second aqueous multi-phase partitioning system). The targeting species may be allowed to bind to or otherwise interact with a virus, e.g., specifically. In some embodiments, binding of the targeting species to the virus alters partitioning of the virus in the partitioning system. This may be useful, for example, to help distinguish a first virus from a second virus, e.g., a coronavirus and an influenza virus. For instance, the targeting species may have a virus-binding moiety (for example, as discussed herein), that is able to recognize only a first virus but not a second virus. Binding of the targeting species to the first virus thus may alter the partitioning behavior of the first virus, but not the second virus, as the second virus is not recognizable (or is recognizable, but to a much lesser extent), by the targeting species. Accordingly, the viruses may exhibit substantially different partitioning behavior in the presence of the targeting species, which can be determined, for example, using agents or techniques such as those described herein. However, it should be understood that a targeting species is not required, and in other embodiments, the viruses may exhibit distinguishable partitioning behavior, i.e., without any targeting species, and/or the agent itself may alter the partitioning behavior, e.g., upon binding to the virus.

Exemplary targeting species may include or comprise, but are not limited to, antibodies (e.g., able to bind to a protein, for example, the proteins described herein for coronaviruses, influenza viruses, etc.), or nucleic acids (e.g., able to bind to nucleic acids, such as RNA or DNA, arising from a virus, e.g., such that the virus-binding moiety comprises a nucleic acid sequence substantially complementary to a portion of the virus's genome). For example, the antibody may be an IgA. Other examples include IgG, IgM, IgD and IgE.

In addition, in some cases, the targeting species may cause aggregation of the viruses. For example, the targeting species may be able to bind to two or more viruses. As an example, the targeting species may include two or more antibodies, nucleic acids, or other species able to bind to a virus.

Figure 2:
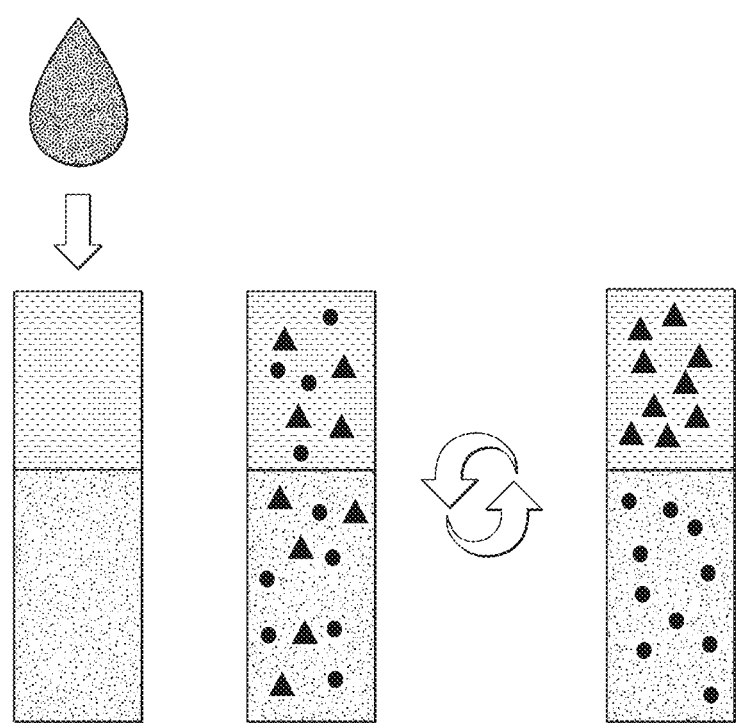
FIG. 2 illustrates an example of a partitioning system for different viruses in one embodiment.

One non-limiting example of such a system can be seen schematically in FIG. 2. In this figure, a partitioning system is shown on the left, and a sample is added. The sample may be, e.g., blood, sputum, saliva, nasal fluid, or other biological fluids such as those described herein. In this example, a two-phase partitioning system is shown as a schematic, although in other embodiments, there may be two or more than two phases.

In this example, the sample may contain two types of viruses, shown schematically as triangles and circles. The triangles represent the virus of interest, while the circles represent other types of viruses (and there may be more than one type of such viruses present in other embodiments). For example, in certain cases, there may be 2, 3, 4, or more contaminating viruses, and/or other entities that are present. Initially, the sample may be randomly distributed between the two phases, although with some mixing, the system may progress towards an equilibrium. This may be facilitated, for example, by agitating the sample in some fashion, e.g., stirring, vortexing, centrifugation, etc. In addition, in some cases, the agitation may be performed by hand. Such agitation may facilitate the distribution of the viruses in the different phases of the partitioning system. This is shown schematically in FIG. 2 as perfect separation (all triangles in the upper phase and all circles in the lower phase), although in reality, the separation need not always be 100% efficient. Lesser amounts of separation are also possible, e.g., as discussed herein. After partitioning of the viruses in the phases, one or more of the phases may be assayed to determine the viruses within those phases, e.g., qualitatively and/or quantitatively (e.g., as a concentration). In some cases, a signaling moiety may be used to facilitate assaying of the viruses. For example, the viruses may be determined colorimetrically, using fluorescence, based on radioactivity, or the like. In certain instances, the assay may be performed using the naked eye (e.g., by determining the viruses colorimetrically), although in some cases, other assay techniques, such as those described herein, may be used to determine the viruses.

Figure 3:
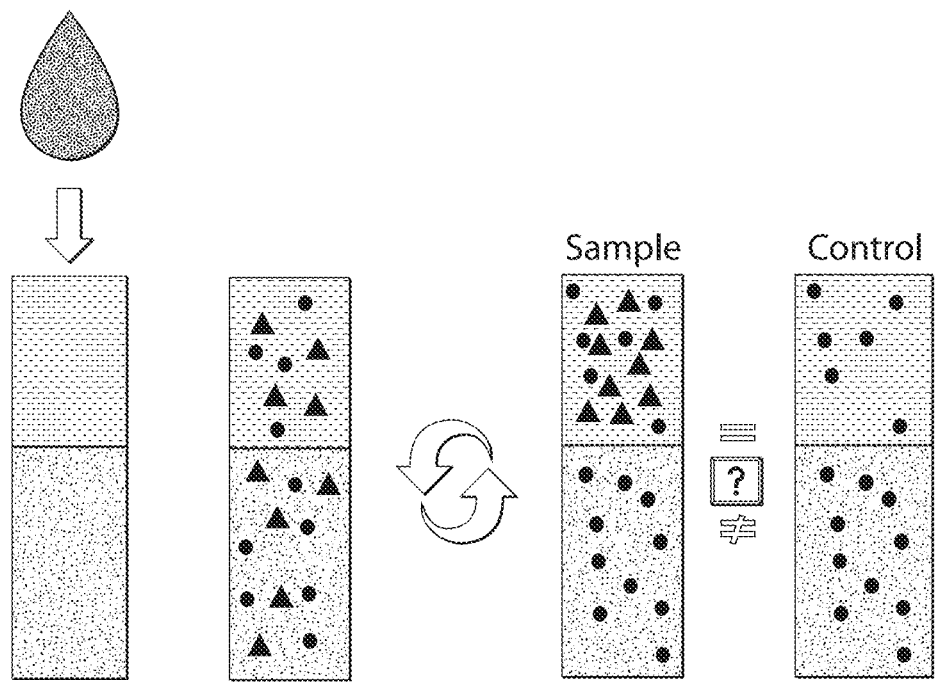
FIG. 3 illustrates another example of a partitioning system which partitions two different viruses differently, in another embodiment.

Another non-limiting example of a system is shown schematically in FIG. 3. In this figure, the viruses (circles) are shown as being unable to partition between the two phases (as is shown in the "control" experiment), although free RNA (triangles) can partition (as is shown in the "sample" experiment).

A variety of techniques may be used to assay the sample. For example, the bottom phase of the experiments may be removed and used to determine whether the viruses of interest are present or not. As another example, the distribution of viruses in an experiment may be determined, with higher concentrations of viruses within the top phase being related to the presence of the virus of interest. In some embodiments, viruses or nucleic acids may be determined in situ, within the partitioning system, i.e., without removing aliquots of one or more of the phases that are used for analysis, although in other embodiments, aliquots of one or more of the phases may be removed from the partitioning system and used to determine viruses, nucleic acids, etc.

It should be understood that although the partitioning was demonstrated as an idealized system, in reality, the partitioning may not be perfect. For example, the sizes of the phases and/or concentrations of viruses within the phases can vary, e.g., where perfect separation or partitioning is not achieved.

Figure 4:
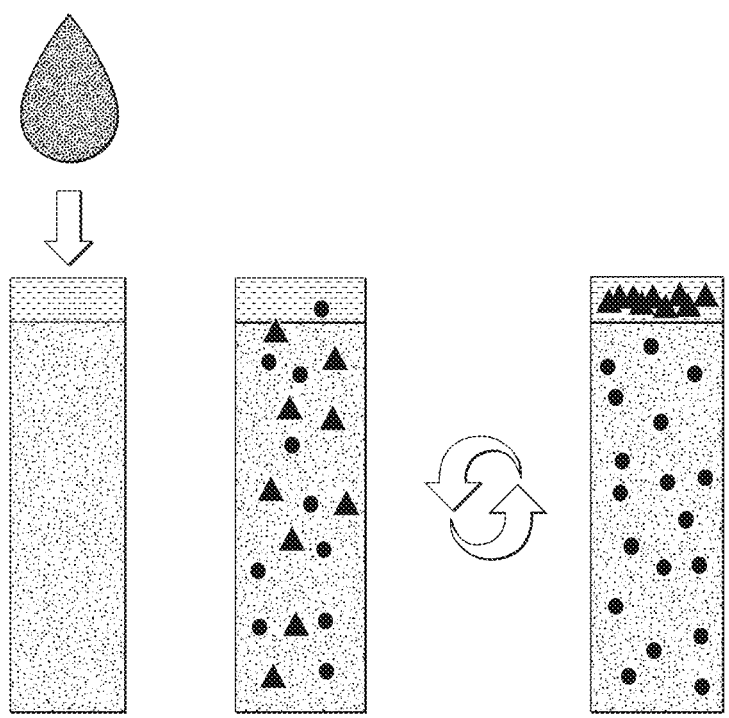
FIG. 4 illustrates another example of a partitioning system in which the phases are not all substantially evenly distributed, in still another embodiment.

As another example, a schematic diagram is shown in FIG. 4 as a non-limiting example. In this case, the top phase is relatively small compared to the bottom phase. This may be useful, for example, where the virus is to be analyzed and/or determined, and/or to facilitate enrichment of the viruses, sample purification, or the like. For example, after using this system, the viruses may be present in a first phase (e.g., the bottom phase), while free RNA may not be concentrated within the first phase along the virus of interest.

Figure 5:
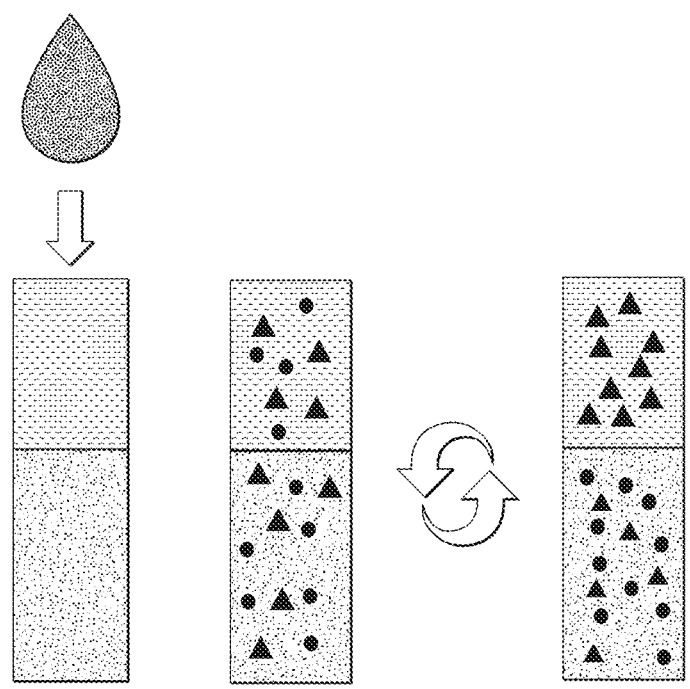
FIG. 5 illustrates yet another example of a partitioning system which partitions nucleic acids to one phase, in yet another embodiment.

As yet another example, a schematic diagram is shown in FIG. 5 as a non-limiting example. In this example, a virus (triangles) is allowed to partition between two phases of a partitioning system, such as an aqueous partitioning system. In contrast, a free nucleic acid (circles), such as DNA or RNA, is preferentially found in one phase of the partitioning system after mixing and equilibration. Accordingly, while the virus is present in both phases, the free nucleic acid is only present in a single phase (in this example, the bottom phase). The top phase may be determined to determine the virus, e.g., without (or with much less) interference from free nucleic acid that may have been present within the sample. For example, the viruses within the top phase may be determined in situ, e.g., within the partitioning system, or aliquots of the top phase may be removed for analysis, e.g., as discussed herein. In addition, in some cases, the bottom phase may also be similarly analyzed, e.g., in situ or using aliquots, for example, to determine the virus and/or free nucleic acids, although it should be understood that this is not a requirement. For instance, in set of embodiments, viruses and/or free nucleic acids may be determined and used to determine a partition coefficient, such as is described herein.

Another aspect of the present disclosure relates to methods and devices for detecting the presence or risk of a disease or condition, e.g., an infection, as related to differential solubility behavior of a virus in the portions or phases of two substantially immiscible liquids. Partitioning systems, including aqueous partitioning systems may be generally employed in some embodiments, wherein the partitioning behavior of a virus is determined. In some cases, different viruses may be distinguished, e.g., as discussed herein.

In some embodiments, a virus can be partitioned in the phases of two (or more) substantially immiscible liquids of a partitioning system, such as an aqueous partitioning system. For example, the two phases of a partitioning system may have different molecular structures in some cases. In equilibrium, differences between the molecular interactions of the virus and the various phases may be determined using the value of a partitioning coefficient between the phases. The value of the partition coefficient for a virus may change, for instance, if the three-dimensional structure of the virus changes.

The chemical ingredients used to prepare a partitioning system that naturally partitions into two or more phases may be selected (e.g., as discussed below) so as to provide this differentiation of behavior as a function of the virus. Once one or more viruses have been partitioned, each phase can be assayed, for example, through immuno-specific assays like ELISA. The viruses may be determined in each phase. A partitioning coefficient, K, may also be determined in some cases from the ratio of concentration of viruses in each phase.

K values for each virus may, in some embodiments, be chosen to be significantly different. For example, K values determined for a subject may be compared to similar ratio values previously determined and recorded for subjects with known health statuses, e.g., infections In one set of embodiments, a virus may be partitioned into the phases (e.g. aqueous phases) of two or more substantially immiscible liquids. Different viruses may differentially partition in each phase. The phases may have different molecular structures. In equilibrium, the differences between the molecular interactions of a virus and the various phases may be manifested through differential solubility of the virus between the phases. In addition, in some cases, the partitioning behavior of a virus may be altered using a targeting species, e.g., as discussed herein.

In some embodiments, only one of the phases (e.g. aqueous phases) is analyzed for concentration, for a virus; no ratio calculation may be used, as the second phase is used for partitioning but not for the assay (however, in other embodiments, more than one of the phases may be analyzed for viral concentrations, as discussed herein).

Preparation of partitioning systems such as those described herein may, in some embodiments, include large-scale robotic screening of chemical ingredients such as soluble polymers, salts, and other additives to cause spontaneous phase separation, e.g., into two or more phases. This screening may be targeted to discover and/or optimize such formulae to distinguish those which could confer differential partitioning of viruses.

In some aspects, a feature for allowing differential solubility for the viruses is a liquid partitioning system. Thus, certain embodiments make use of a liquid partitioning system for use in the detection of a disease or condition in a subject, including: two or more liquid phases, the liquid phases being substantially immiscible. In some cases, some or all of the liquid phases may have an aqueous component. In some embodiments, a plurality of species associated with the disease or condition can be solubilized. In some cases, the concentrations of a virus in a phase may be related to the presence or absence of the disease or condition in the subject.

Typical, but non-limiting, components of the aqueous phases include at least one of polyethylene glycol, dextran, polyvinyleperrolidone, Ficoll®, and copolymer of ethylene glycol and propylene glycol. The liquid partitioning system may include, in some embodiments, substantially immiscible phases, where some or all of the phases may have an aqueous component. The virus may interact differently with the chemicals (and water) of each layer, and thus dissolve or partition differentially. Liquid partitioning systems, including aqueous liquid partitioning systems and various compositions for forming such systems, are discussed in greater detail herein. However it should be noted that the disclosure is not limited to only liquid-liquid partitioning, e.g., as described above, but also encompasses, in other embodiments, chromatography (e.g., liquid-liquid partition chromatography), heterogeneous two-phase systems, or multi-phase heterogeneous systems), and other suitable techniques for generating a partition coefficient or at least an apparent partition coefficient.

In addition, in accordance with certain aspects of the present disclosure, the state of a molecule, such as a virus, can be affected by many different factors including, but not limited to, changes in the structure of the virus, interactions with one or more other biomolecules or ligands, and the like. Evaluation of different states can be used as one method of determining the potential effectiveness of different potential species on the virus, etc.

In addition, in some cases, partitioning of the virus in the partitioning system may be surprisingly rapid. For example, in some cases, substantial partitioning may occur in less than 1 hour, less than 30 minutes, less than 15 minutes, less than 10 minutes, less than 5 minutes, less than 3 minutes, less than 2 minutes, or less than 1 minute. In some cases, within these times, sufficient partitioning may have occurred to allow for determination of the virus as discussed herein, e.g., in one or more phases of the partitioning system. For example, within these times, partitioning of the virus can be determined colorimetrically or with the naked eye, etc.

In some aspects, a phase of the partitioning system may be removed, and optionally transferred to a second partitioning system. The second partitioning system may include any of the systems described herein, and may be the same or different than the first partitioning system.

In one set of embodiments, one or more of the phases of a partitioning system may contain a virus, which can be determined, e.g., as discussed herein. In some cases, the virus may be denatured, e.g., to release nucleic acid from the virus into the partitioning system, e.g., for determination. For example, the nucleic acid may comprise DNA and/or RNA. For example, to release nucleic acid, the virus can be exposed to a denaturing agent, alkaline hydrolysis, Iso-Quick, lysis buffer in conjunction with proteinase K, phenol-chloroform extraction followed by ethanol precipitation, solvent or detergent inactivation (e.g., using Triton X-100), pasteurization (heating, e.g., to temperatures of at least 60° C., at least 70° C., at least 80° C., at least 90° C., etc.), acidic (low pH) inactivation, or other techniques known to those of ordinary skill in the art.

In yet another set of embodiments, various systems and methods such as those discussed herein can be used to purify a sample of biological fluid. In some cases, the sample of biological fluid may be from a subject, such as a subject suspected of having or being exposed to a specific viral disease. For example, in one embodiment, free nucleic acids may be removed from a sample using a partitioning system, such as is described herein.

In some cases, systems and methods such as those discussed herein may be used prior to other tests such as those described herein, for example, identification tests such as polymerase chain reaction (PCR), sequencing techniques including those described herein, or the like. This may be important, for example, in applications when a sample may potentially be contaminated, e.g., with closely related RNA or DNA material from similar viral families, or to distinguish between different types of viruses (e.g., coronavirus versus influenza virus), etc. In certain embodiments, as a non-limiting example, a virus or viral component of interest from a sample may be partitioned into, or at least partially enriched in, one phase of a partitioning system (e.g., an aqueous multi-phase partitioning system), while other matter may be partitioned into a different phase. The phase containing or being enriched in the virus or other viral component of interest (e.g., RNA, such as free RNA) may then in some cases be used for identification or sequencing tests, etc., such as those described herein.

In some embodiments, free RNA or other nucleic acids may be concentrated in one phase of a partitioning system (e.g., an aqueous multi-phase partitioning system) by selecting properties of the partitioning system such that the volume ratio between that phase and the other phase(s) will be large. For example, a partitioning system may be selected to have a volume ratio of the two phases to be 1:1 or more, 1:2 or more, 1:3 or more, 1:5 or more, 1:10 or more, 1:20 or more, 1:50 or more, or even larger, where the smaller volume is the phase containing or being enriched in free nucleic acids. In some cases, substantially all of the free nucleic acids may be present in one phase of the partitioning system. According to certain embodiments, the presence of substantially all the free nucleic acids in one or more phase of the partitioning system may mean that greater than or equal to 80%, greater than or equal to 85%, greater or equal to 90%, greater than or equal to 95%, or greater than or equal to 97.5% of the free nucleic acids may be found within that one or more phase.

In certain cases, a virus may be determined by determining a nucleic acid originating from the virus. For example, a virus may be denatured, e.g., as discussed herein, to release a nucleic acid from the interior of the virus. Those of ordinary skill in the art will be able to determine the nucleic acid, for example, using antibodies that bind to nucleic acid, or the like. The nucleic acid may be determined colormetrically, for example. In some cases, signaling moieties may be attached to nucleic acid-binding entities to facilitate detection, e.g., within the partitioning system. For example, signaling moieties that bind to nucleic acids can be used to determine partitioning. Non-limiting examples of signaling moieties include ethidium bromine or ethidium monoazide bromide, cyanine dyes (e.g. Cy3, Cy5, etc.), propidium iodide, crystal violet, dUTP-conjugated probes, DAPI (4',6-diamidino-2-phenylindole), 7-AAD (7-aminoactinomycin D), Hoechst 33258, Hoechst 33342, Hoechst 34580, YOYO-1, DiYO-1, TOTO-1, DiTO-1, etc. Other examples of signaling moieties include those discussed herein.

In addition, in some cases, the nucleic acid may be sequenced. Examples of sequencing techniques known to those of ordinary skill in the art include, but are not limited to, Sanger methods or other suitable techniques, chain-termination sequencing, sequencing-by-hybridization, Maxam-Gilbert sequencing, dye-terminator sequencing, chain-termination methods, Massively Parallel Signature Sequencing (Lynx Therapeutics), polony sequencing, pyrosequencing, sequencing by ligation, ion semiconductor sequencing, DNA nanoball sequencing, single-molecule real-time sequencing, nanopore sequencing, microfluidic Sanger sequencing, digital RNA sequencing ("digital RNA-seq"), etc.

In some cases, such signaling moieties such as those described herein may be determined unaided, e.g., to the naked eye, although detectors such as those described may be used in certain embodiments. Non-limiting examples of suitable detectors include microscopes (e.g., fluorescence microscopes), plate readers, ELISA readers, etc. In some cases, the signaling moiety may be colorimetrically determined.

As another non-limiting example, a signaling moiety may comprise a particle. The particles may be nanoparticles, such as gold nanoparticles, that, in some embodiments are, coated with a virus-binding moiety, such as RNA. These can be mixed, e.g., in situ, with a partitioning system containing viruses or other viral material. Upon hybridization with target viral nucleic acids in a partitioning system, a color change may be used to indicate presence of a specific target viral nucleic acid. This may be, in some embodiments, at high specificity due to the hybridization specificity of the nanoparticles. In addition, in some cases, e.g., if one phase of the partitioning system is enriched in the target viral nucleic acid, the color change may be relatively concentrated in one phase of the partitioning system. Thus, a color change specific to one phase in the partitioning system may be used to determine the target viral nucleic acids. In addition, in some cases, the degree of color change may be used to determine concentrations. In some cases, this dual-specificity test may reach the diagnostic specificity of PCR with the speed and simplicity of other colorimetric screening assays.

In some cases, a targeting species may be used. Non-limiting examples include targeting species such as those described herein. For example, the targeting species may cause aggregation of the viruses.

Particles may be of any suitable size. For example, particles may have a diameter of greater than or equal to 10 nm, greater than or equal to 50 nm, greater than or equal to 100 nm, greater than or equal to 500 nm, greater than or equal to 1 micrometer, or greater. In some embodiments, particles have a diameter of less than or equal to 5 micrometers, less than or equal to 1 micrometer, less than or equal to 500 nm, less than or equal to 100 nm, or less. Combinations of these ranges are possible. For instance, in some embodiments, particles may have a diameter that is greater than or equal to 10 nm and less than or equal to 5 micrometers.

Particles as described herein may comprise any suitable material. In some embodiments, particles may comprise metals. For example, particles may comprise gold, silver, titanium, or any other suitable material. Particles may also comprise polymers or ceramic materials appropriate for a given embodiment.

In addition, according to some aspects of the present disclosure, a computer and/or an automated system is provided able to automatically and/or repetitively perform any of the methods described herein. As used herein, "automated" devices refer to devices that are able to operate without human direction, i.e., an automated device can perform a function during a period of time after any human has finished taking any action to promote the function, e.g. by entering instructions into a computer. Typically, automated equipment can perform repetitive functions after this point in time. One specific example of a technique that can make use of a computer or other automated system is in a process in which a physiological condition of a system as determined by determining a relative measure of interaction between one or more species from a sample from the system and various interacting components of a partitioning system. In the clinical setting, this may be accomplished by drawing a sample of blood (milliliter-sized or a very small sample such as a drop or less) and subjecting the blood sample or a subset thereof (e.g., plasma) to a multi-phase partitioning process. The results of this process can then be compared to similar behavior of markers in a similar system, which can take the form of data stored electronically.

Various embodiments of the present disclosure can also be implemented exclusively in hardware, or in a combination of software and hardware. For example, in one embodiment, rather than a conventional personal computer, a Programmable Logic Controller (PLC) is used. As known to those skilled in the art, PLCs are frequently used in a variety of process control applications where the expense of a general purpose computer is unnecessary. PLCs may be configured in a known manner to execute one or a variety of control programs, and are capable of receiving inputs from a user or another device and/or providing outputs to a user or another device, in a manner similar to that of a personal computer. Accordingly, although embodiments of the present disclosure are described in terms of a general purpose computer, it should be appreciated that the use of a general purpose computer is exemplary only, as other configurations may be used.

"Aqueous," as used herein, refers to the characteristic properties of a solvent/solute system wherein the solvating substance has a predominantly hydrophilic character. Examples of aqueous solvent/solute systems include those where water, or compositions containing water, are the predominant solvent.

"Partitioning system," as used herein, refers to any material having at least two phases, sections, areas, components, or the like, at least two of which can interact differently with at least one species to which they are exposed. For example, a partitioning system can include different areas of a solid surface, which can interact differently with a particular molecule exposed to the different sections, a multi-phase system such as a multi-phase liquid system, e.g., an aqueous/non-aqueous system or an aqueous multi-phase system (as defined herein) to which one or more species can be exposed and optionally dissolved, at least some of which species can interact differently with different phases. For example, a particular species may have a greater affinity for one phase rather than another phase to the extent that a multi-phase partitioning system can isolate a species from a mixture, or cause a species to partition at least in some way differently between the phases.

"Aqueous multi-phase system," as used herein, refers to an aqueous system which includes greater than one aqueous phase in which a species can reside, and which can be used to characterize the structural state of the species according to the methods described herein. For example, an aqueous multi-phase system can separate at equilibrium into two, three, or more immiscible phases. Aqueous multi-phase systems are known in the art and this phrase, as used herein, is not meant to be inconsistent with accepted meaning in the art. Examples of various aqueous multi-phase systems, and their compositions, are discussed herein.

An "interacting component" means a component, such as a phase of multi-phase system, that can interact with a species and provide information about that species (for example, an affinity for the species). Multiple interacting components, exposed to a species, can define a system that can provide a "relative measure of interaction" between each component and the species. An interacting component can be aqueous or non-aqueous, can be polymeric, organic (e.g. a protein, small molecule, etc.), inorganic (e.g. a salt), or the like, or any combination thereof. A set of interacting components can form a system useful in and in part defining any experimental method which is used to characterize the structural state of a species according to the methods described herein. Typically, a system of interacting components can measure the relative interaction between the species and at least two interacting components. An aqueous multi-phase system is an example of a system of interacting components, and it is to be understood that where "aqueous system" or "aqueous multi-phase system" is used herein, this is by way of example only, and any suitable system of interacting components can be used.

Where aqueous two-phase and aqueous multi-phase systems are described herein, it is to be understood that other systems, as used herein, systems analogous to those comprising only aqueous solutions or suspensions can be used. For example, an aqueous two-phase system can include non-aqueous components in one or more phases that are not liquid in character. In this aspect, multi-phase systems also refers to related techniques that rely on differential affinity of the biomolecule to one media versus another, wherein the transport of the biomolecule between one medium and, optionally, another medium occurs in an aqueous environment. Examples of such multi-phase systems include, but are not limited to, HPLC columns or systems for liquid-liquid partition chromatography, as are known to those of ordinary skill in the art.

"Relative measure of interaction," with reference to a particular species as used herein, means the degree to which the species interacts with another species or with a phase of a multi-phase system in a relative sense. For example, a particular species may have a greater affinity for one phase of a multi-phase system rather than another phase or phases, the degree to which it interacts with or resides in, that phase as opposed to other phases defines its relative measure of interaction. Relative measures of interaction, in the context of the present disclosure, are generally determined in a ratiometric manner, rather than an absolute manner. That is, where a species can interact with each phase of a two-phase system but resides more preferably in one than the other, the present disclosure typically makes use of information as to the ratio of concentration of the species in each of the two phases, but not necessarily of the absolute concentration of the species in either phase. In other cases, the interaction can be an interaction based not upon residence of a particular species within a particular solvent or fluid carrier, but interaction with a solid surface such as a solid phase of a chromatography column where the relative measure manifests itself in elution time, or can involve geometric or spatial interaction such as a particular species interaction with a porous substrate as opposed to that of a different species or a different substrate.

"Partition coefficient," as used herein, refers to the coefficient which is defined by the ratio of chemical activity or the concentrations of a species in two or more phases of a multi-phase system at equilibrium. For example, the partition coefficient (K) of a species in a two-phase system can be defined as the ratio of the concentration of species in the first phase to that in the second phase. For multi-phase systems, there can be multiple partition coefficients, where each partition coefficient defines the ratio of species in first selected phase and a second selected phase. It will be recognized that the total number of partition coefficients in any multi-phase system will be equal to the total number of phases minus one.

For heterogeneous phase systems, an "apparent partition coefficient," as used herein, refers to a coefficient which describes information obtained from alternative techniques that is correlated to the relative partitioning between phases. For example, if the heterogeneous two-phase system used is an HPLC column, this "apparent partition coefficient" can be the relative retention time for the species. It will be recognized by those of ordinary skill in the art that the retention time of a species, in such a case, reflects the average partitioning of the species between a first, mobile phase and a second, immobile phase. Also, it will be recognized that other, similarly determinable properties of species can also be used to quantify differences in physical properties of the species (e.g. in other techniques) and are, therefore, suitable for use as apparent partition coefficients.

"Bind," as used herein, means the well-understood receptor/ligand binding, as well as other nonrandom association between a biomolecule and its binding partner. "Specifically bind," as used herein, describes a binding partner or other ligand that does not cross react substantially with any biomolecule other than the biomolecule or biomolecules specified. Generally, molecules which preferentially bind to each other are referred to as a "specific binding pair." Such pairs include, but are not limited to, an antibody and its antigen, a lectin and a carbohydrate which it binds, an enzyme and its substrate, and a hormone and its cellular receptor. As generally used, the terms "receptor" and "ligand" are used to identify a pair of binding molecules. Usually, the term "receptor" is assigned to a member of a specific binding pair, which is of a class of molecules known for its binding activity, e.g., antibodies. The term "receptor" is also preferentially conferred on the member of a pair that is larger in size, e.g., on lectin in the case of the lectin-carbohydrate pair. However, it will be recognized by those of skill in the art that the identification of receptor and ligand is somewhat arbitrary, and the term "ligand" may be used to refer to a molecule which others would call a "receptor." The term "anti-ligand" is sometimes used in place of "receptor."

"Molecule-molecule interaction," such as biomolecule-biomolecule interaction, protein-protein interaction, and the like means an interaction that typically is weaker than "binding," i.e., an interaction based upon hydrogen bonding, van der Waals binding, London forces, and/or other non-covalent interactions that contribute to an affinity of one molecule for another molecule, which affinity can be assisted by structural features such as the ability of one molecule to conform to another molecule or a section of another molecule. Molecule-molecule interactions can involve binding, but need not.

"Biomolecule," as used herein, means a molecule typically derived from a subject, and which typically includes building blocks including nucleotides, and the like. Examples include, but are not limited to, peptides, polypeptides, proteins, protein complexes, nucleotides, oligonucleotides, polynucleotides, nucleic acid complexes, saccharides, oligosaccharides, carbohydrates, lipids, etc., as well as combinations, enantiomers, homologs, analogs, derivatives and/or mimetics thereof.

"Species," as used herein, refers to a molecule or collection of molecules, for example, an inorganic chemical, an organic chemical, a biomolecule, or the like. In the present disclosure, species generally are biomolecules.

"Corresponding species," as used herein, means at least two different species that are identical chemically or, if they differ chemically and/or by molecular weight, differ only slightly. Examples of corresponding species include structural isoforms of proteins, proteins or other molecules that are essentially identical but that differ in binding affinity with respect to another species or plural species, have different higher-order structure, e.g., differing in secondary or tertiary structure but not differing or not differing significantly in chemical sequence. In general, corresponding species are species that may be arranged differently (isoforms, isomers, etc.) but are composed of the same or essentially the same chemical building blocks.

"Detectable," as used herein, refers the ability of a species and/or a property of the species to be discerned. One example method of rendering a species detectable is to provide further species that bind or interact with the first species, where the species comprise(s) a detectable label. Examples of detectable labels include, but are not limited to, nucleic acid labels, chemically reactive labels, fluorescence labels, enzymatic labels and radioactive labels.

"Mimetic," as used herein, includes a chemical compound, an organic molecule, or any other mimetic, the structure of which is based on, or derived from, a binding region of an antibody or antigen. For example, one can model predicted chemical structures to mimic the structure of a binding region, such as a binding loop of a peptide. Such modeling can be performed using standard methods (see, for example, Zhao et al., *Nat. Struct. Biol.* 2: 1131-1137 (1995)). The mimetics identified by methods such as this can be further characterized as having the same binding function as the originally identified molecule of interest, according to the binding assays described herein.

"Structure," "structural state," "configuration" or "conformation," as used herein, all refer to the commonly understood meanings of the respective terms, for example, as they apply to biomolecules such as proteins and nucleic acids, as well as pharmacologically active small molecules. In different contexts, the meaning of these terms will vary, as is appreciated by those of skill in the art. The structure or structural state of a molecule refers generally not to the building blocks that define the molecule but the spatial arrangement of these building blocks. The configuration or confirmation typically defines this arrangement. For instance, the use of the terms primary, secondary, tertiary or quaternary, in reference to protein structure, have accepted meanings within the art, which differ in some respects from their meaning when used in reference to nucleic acid structure (see, e.g., Cantor and Schimmel, *Biophysical Chemistry*, Parts I-III). Unless otherwise specified, the meanings of these terms will be those generally accepted by those of skill in the art.

"Physiological conditions," as used herein, means the physical, chemical, or biophysical state of a subject. As most typically used in the context of the present disclosure, physiological condition refers to a normal (e.g., healthy in the context of a human) or abnormal (e.g., in a diseased state in the context of a human) condition.

"Marker," as used herein, is a species that can be a carrier of information regarding a physiological state of a biological environment within which it resides. A marker can exhibit at least two different properties or values of a specific property or properties (e.g., structural conformation, binding affinity for another species, etc. but not solely different amounts of the species) that correspond to and/or that represent information regarding the two or more physiological states of environments within which they reside. For example, a marker may be a protein that is structurally modified between a first state representative of a healthy system within which it resides and a second structural state (different conformation) representative of a disease system within which it resides.

The following documents are incorporated herein by reference: U.S. Pat. No. 7,968,350, issued Jun. 28, 2011, entitled "Characterization of Molecules"; U.S. Pat. No. 8,099,242, issued Jan. 17, 2012, entitled "Systems and Methods for Characterization of Molecules"; International Patent Application No. PCT/US04/019343, filed Jun. 14, 2004, entitled "Systems and Methods for Characterization of Molecules," published as Int. Pat. Apl. Pub. No. WO 2004/111655 on Dec. 23, 2004; U.S. Pat. Apl. Pub. No. 2015-0219655, entitled "Methods and Devices for Analyzing Species to Determine Diseases"; U.S. patent application Ser. No. 62/987,385, filed May 10, 2020, entitled "Systems and Methods for Determining Viruses such as Coronaviruses"; U.S. patent application Ser. No. 62/982,880, filed Feb. 28, 2020, entitled "Systems and Methods for Determining Viruses such as Coronaviruses"; U.S. patent application Ser. No. 62/987,385, filed Mar. 10, 2020, entitled "Systems and Methods for Determining Viruses such as Coronaviruses"; U.S. patent application Ser. No. 63/071,472, filed Aug. 28, 2020, entitled "Systems and Methods for Determining Viruses such as Coronaviruses"; U.S. patent application Ser. No. 63/091,849, filed Oct. 14, 2020, entitled "Systems and Methods for Determining Viruses such as Coronaviruses"; U.S. patent application Ser. No. 63/000,441, filed Mar. 26, 2020, entitled "Determination of Viruses such as Coronaviruses Based on Viral Proteins"; and U.S. patent application Ser. No. 63/003,843, filed Apr. 1, 2020, entitled "Determination of Viruses such as Coronaviruses Based on Viral Proteins." In addition, U.S. Provisional Patent Application Ser. No. 63/162,485, filed Mar. 17, 2021, entitled "RNA Separation and Related Techniques for Determining Viruses such as Coronaviruses," by Chait, et al., is also incorporated herein by reference in its entirety.

The following examples are intended to illustrate certain embodiments of the present disclosure, but do not exemplify the full scope of the disclosure.

Example 1

This example illustrates the partitioning of RNA based primarily on its negative charge exclusively into one phase of an aqueous two-phase system (ATPS).

The following aqueous two-phase systems where prepared.

ATPS 1: An aqueous two-phase system was prepared with dextran-75 (with an average molecular weight of 75,000), polyethylene glycol PEG-8000 (with an average molecular weight of 8,000), 0.15 M NaCl, and 0.01 M sodium phosphate buffer (NaPB), pH 7.4.

ATPS 2: An aqueous two-phase system was prepared with dextran-75 (with an average molecular weight of 75,000), polyethylene glycol PEG-8000 (with an average molecular weight of 8,000), and 0.09 M NaCl, and 0.05 M sodium phosphate buffer (NaPB), pH 7.4.

ATPS 3: An aqueous two-phase system was prepared with dextran-75 (with an average molecular weight of 75,000), polyethylene glycol PEG-8000 (with an average molecular weight of 8,000), and 0.11 M sodium phosphate buffer (NaPB), pH 7.4.

ATPS 4: An aqueous two-phase system was prepared with Ficoll®-70 (with an average molecular weight of 70,000), polyethylene glycol PEG-8000 (with an average molecular weight of 8,000), and 0.01 M sodium phosphate buffer (NaPB), pH 7.4.

ATPS 5: An aqueous two-phase system was prepared with Ficoll®-70 (with an average molecular weight of 70,000), polyethylene glycol PEG-8000 (with an average molecular weight of 8,000), 1.00 M TMAO and 0.01 M sodium phosphate buffer (NaPB), pH 7.4.

ATPS 6: An aqueous two-phase system was prepared with Ficoll®-70 (with an average molecular weight of 70,000), Polyethylene glycol PEG-8000 (with an average molecular weight of 8,000), 1.50 M TMAO and 0.01 M sodium phosphate buffer (NaPB), pH 7.4.

Partitioning of RNA Standard. RNA standard, a transcript of kanamycin resistance gene with 1200 bp (medium size), standard component of The QuantiFluor® RNA System (Lot 454662) supplied by Promega, that allows accurate detection of RNA over a broad dynamic range, was used as sample. The RNA standard (25 microliters of 100 micrograms/mL) and the corresponding amount (163 microliters, respectively) of 1× PBS were added to the system. A blank system was prepared for comparison. The systems were shaken and centrifuged for 30 min at 3,500 RPM (1160 g) in a refrigerated centrifuge (Universal 320R, Hettich, Germany) with a microplate rotor with the temperature maintained at 23° C. to speed phase settling. Microtubes were taken out of the centrifuge, and aliquots of 75 microliters from the top and the bottom phases were withdrawn for analysis using The QuantiFluor® RNA System. The QuantiFluor® RNA System was used to quantify the concentration of RNA. Both phases were diluted 3-fold with 1×TE Buffer (The QuantiFluor® RNA System diluent), mixed and 10 microliters transferred, in duplicate, to a fluorescent microplate containing 200 microliters/well of The QuantiFluor® RNA Dye working solution (diluted 1:400 in 1×TE Buffer). The plate was mixed thoroughly using a plate shaker, then the assay incubated for 5 minutes at room temperature while mixing protected from light and the fluorescence (492 $nm_{Ex}$/540 $nm_{Em}$) measured using the plate reader (FLUOstar Omega microplate reader, BMG LABTECH, N.C., USA).

RNA Partitioning. The partition coefficient for RNA Standard was determined as the ratio of the top to bottom phase concentrations (in FU) and the results presented in the following table (average of 2 repeats).

| ATPS ID | Sample ID | Top, Av. FU | Bottom, Av. FU |
|---|---|---|---|
| 1 | Blank | 447 | 450 |
| 1 | RNA | 455 | 3430 |
| 2 | Blank | 408 | 437 |
| 2 | RNA | 442 | 3466 |
| 3 | Blank | 391 | 399 |
| 3 | RNA | 396 | 3213 |
| 4 | Blank | 413 | 661 |
| 4 | RNA | 432 | 3391 |
| 4 + 0.38M $MgCl_2$ | Blank | 417 | 629 |
| 4 + 0.38M $MgCl_2$ | RNA | 438 | 1500 |
| 4 + 0.5M $MgCl_2$ | Blank | 438 | 598 |
| 4 + 0.5M $MgCl_2$ | RNA | 410 | 1171 |
| 5 | Blank | 348 | 509 |
| 5 | RNA | 365 | 3072 |
| 6 | Blank | 366 | 537 |
| 6 | RNA | 389 | 2837 |

The above example thus illustrates the negatively charged RNA partitioned generally to one phase of aqueous two phase partitioning systems.

Example 2

This example illustrates partitioning of RNA based primarily on its negative charge exclusively into the bottom phase of an Aqueous Two-Phase System (ATPS), with a system shown to partition SARS-CoV-2 whole virions into both top and bottom phases, therefore allowing direct detection of whole virions by detecting its RNA via subsequent molecular testing of only the top phase.

An aqueous two-phase system was prepared with Dextran-75 (Lot 119945) with an average molecular weight of 75,000 supplied by USB, polyethylene glycol PEG-8000 (Lot SLBW6815) with an average molecular weight of 8000 purchased from Sigma, and sodium phosphate buffer (NaPB), pH 7.4. Appropriate amounts of polymers and NaPB, pH 7.4 stock solutions were dispensed into a 1.2 mL microtube using Hamilton (Reno, Nev., USA) ML-4000 four-probe liquid handling workstation for the final system (after sample addition, see below) with a total weight of 0.5 g (total volume of ca. 466 microliters).

Partitioning of RNA Standard. RNA standard, a transcript of kanamycin resistance gene with 1200 bp (medium size), standard component of The QuantiFluor® RNA System (Lot 454662) supplied by Promega, that allows accurate detection of RNA over a broad dynamic range, was used as sample. The RNA standard (25 microliters of 100 micrograms/mL) and the corresponding amount (163 microliters, respectively) of 1× PBS were added to the system. A blank system was prepared for comparison. The systems were shaken and centrifuged for 30 min at 3500 RPM (1160 g) in a refrigerated centrifuge (Universal 320R, Hettich, Germany) with a microplate rotor with the temperature maintained at 23° C. to speed phase settling. Microtubes were taken out of the centrifuge, and aliquots of 75 microliters from the top and the bottom phases were withdrawn for analysis using The QuantiFluor® RNA System. The QuantiFluor® RNA System was used to quantify the concentration of RNA. Both phases were diluted 3-fold with 1×TE Buffer (The QuantiFluor® RNA System diluent), mixed and 10 microliters transferred, in duplicate, to a fluorescent microplate containing 200 microliters/well of The QuantiFluor® RNA Dye working solution (diluted 1:400 in 1×TE Buffer). The plate was mixed thoroughly using a plate shaker, then the assay incubated for 5 minutes at room temperature while mixing protected from light and the fluorescence (492 $nm_{Ex}$/540 $nm_{Em}$) measured using the plate reader (FLUOstar Omega microplate reader, BMG LABTECH, N.C., USA).

RNA Partitioning. The partition coefficient for RNA Standard was determined as the ratio of the top to bottom phase concentrations (in FU) and the results presented in the following table (average of 2 repeats). The RNA was present only in the bottom phase. This RNA standard was partition to the bottom phase because of its negative charge, a property shared with other negatively charged RNA.

| Sample ID | Top, Av. FU | Bottom, Av. FU | K (FU) = T/B |
|---|---|---|---|
| Blank | 391 | 399 | K < 1 (0.002) |
| RNA std | 396 | 3213 | |

Whole Virion Partitioning. The virus tested was SARS-CoV-2 UTHSC passage 3, (SARS-Related Coronavirus 2 Isolate USA-WA1/2020), and H1N1 (PR8). The titer of the stock viruses was $2\times10^6$ pfu/mL SARS CoV-2, and $1\times10^8$ pfu/mL, PR8. The inoculum of the viruses was $4\times10^4$ pfu, SARS CoV-2 and PR8. The cell line for the plaque assays were Vero E6 (SARS CoV2) and MDCK (PR8).

The standard plaque assays were conducted with aliquots taken from the top and bottom phases, as follows:

| Top phase pfu | Dilution factor | Top pfu/ml | Bottom phase pfu | Dilution factor | Bottom pfu/ml |
|---|---|---|---|---|---|
| 20 | 2 | 200 | 44 | 2 | 440 |

The above results demonstrated that if, e.g., a clinical sample containing both whole virions of SARS-CoV-2 and free RNA of the same virus (dead viruses), as well as other biological matter, were to be tested, obtaining an aliquot of the top phase only following partitioning and then using a molecular test specific to the virus RNA such as RT-PCR, the presence or absence of whole virions in the original sample would have been detected directly.

Example 3

This example provides results from a validation study of one of the embodiment to determine the infectivity potential of a clinical sample obtained from a patient suspected of carrying a virus.

Patients suspected SARS-CoV-2 infection at Cleveland Clinic were screened by nasopharyngeal swab into saline, UTM or VTM, followed by RT-PCR (Roche Diagnostics COBAS 8800) targeting the ORF1 a/b non-structural region and the E envelope region with a limit of detection (Ct) of about 35. The remaining sample of patients determined as PCR positive were aliquoted into two or more separate tubes. A 400 microliter aliquot of the sample was added into each of two tubes containing An ATPS system comprising Dextran-75 (with an average molecular weight of 75,000), polyethylene glycol PEG-8000 (with an average molecular weight of 8,000), and 0.11 M sodium phosphate buffer (NaPB), pH 7.4 was used. The tubes were sealed, gently mixed by inversion 25× times, and span in a mini-centrifuge for 1 minute until phase separation. Aliquots (350 microliters) from the top phase were added to 100 microliters of PBS and mixed and followed by a standard RT-PCR protocol as described above.

The Roche Cobas® 8800 system is a fully enclosed and automated PCR system with HEPA inline filters for contamination control for running Cobas® SARS-CoV-2 and Influenza A/B assays based on fully automated sample preparation (nucleic acid extraction and purification) followed by PCR amplification and detection. Target-specific forward and reverse primers are used for ORF1a/b non-structural region that is unique to SARS-CoV-2 as well as the E gene in the envelope. The following table outlines the results interpretation, with Target 1 being the ORF 1 a/b and Target 2 being the E gene.

| Target 1 | Target 2 | Interpretation |
|---|---|---|
| Positive | Positive | All Target Results were valid. Result for SARS-CoV-2 RNA is Detected. |
| Positive | Negative | All Target Results were valid. Result for SARS-CoV-2 RNA is Detected. |
| Negative | Positive | All Target Results were valid. Result for SARS-CoV-2 RNA is Presumptive Positive. Sample will be resulted as Positive with a comment (see result reporting section) |

The results from RT-PCR analysis of the top phase aliquot were interpreted as follows:

1. For Ct greater than the limit of detection of the assay (35 for the Roche COBAS 8800), no whole virus particles were detected in the sample.
2. For Ct less than the limit of detection, whole virus particles were detected in the sample, potentially marking the patient as capable of transmitting the virus (depending on the type of virus and mode of transmission, e.g., via aerosol for SARS-CoV-2).

Samples from the original collection tubes separated prior to the ATPS assay were sent for virus culture in a high biosafety laboratory at the United States Army Medical Research Institute of Infectious Diseases (Ft. Detrick, Md.) for a PCR-based infection assay to serve as a gold-standard for validation of predictions of presence or absence of whole functional virus particles in the original samples.

ATCC Vero76 cells were seed in 24 well plates and were ~100% confluent at the start of the experiment. Samples were diluted in growth media at a 1:100 ratio. Media was decanted from the plate, and the viral innoculums were added. For a negative control, only media was added to wells whereas the positive control consisted of a 1:100 innoculum of the WA-1/2020 SARS2 isolate previously mentioned. This positive control input equated to a viral input of $7.19 \times 10^3$ PFU/mL, or 3595 PFU/well. Cells were then incubated at 37° C./5% $CO_2$ for two days, at which point 200 microliters of supernatant was harvested from wells and inactivated with a 3:1 ratio of TRIzol LS. The initial inoculum was also prepared as a TRIzol LS sample in an identical fashion, and represented the day 0 time point sample. Samples were prepared in biological duplicates.

TRIzol LS-inactivated supernatants were extracted with an EZ1 Advanced extraction robot using the virus mini 2.0 extraction kit following manufacturer's recommendations. All extracted samples were then analyzed with a previously reported RT-PCR assay designed to detect the SARS2 E gene. Reactions were run on the LightCycler 480 (Roche) with the following cycling conditions: 50° C. for 10 min (1 cycle); 95° C. for 3 min (1 cycle); 95° C. for 10 s/56° C. for 15 s/72° C. for 5 s (45 cycles); and 40° C. for 30 s (1 cycle). A single fluorescence read was taken at the end of each 72° C. step, and a sample was considered positive if the Ct value was less than 40 cycles. Samples were assayed in technical triplicate, and the Ct's were averaged. Day 2 Ct values were then subtracted from Day 0 values to determine the change in Ct ($\Delta$Ct), and if this value was a positive value (namely, Ct at Day 2 was lower than that in Day 0), the interpretation was that a functional virus was replicating in the sample and the interpretation was declared as positive or infective. Conversely, if the change in Ct ($\Delta$Ct) was negative or zero, no growth was observed and the sample was declared as negative for functional virus content or non-infective. A synthetic RNA template representing the SARS2 E gene target sequence was utilized as a positive control. The limit of detection for this assay is approximately 10,000 genome copies/mL. The prediction results from the ATPS results and the confirmatory culture results from several experiments are illustrated in the table below.

| Sample ID | PCR Taq Path E | PCR Taq Path ORF 1 | ATPS Predictive Interpretation | Day 0 Ct Validation | Day 2 Ct Validation | Validation Interpretation |
|---|---|---|---|---|---|---|
| CDX025 | — | — | Negative | — | — | Negative |
| CDX028 | 32.03 | 32.44 | Positive | 30.54 | 30.3 | Positive |
| CDX030 | 31.13 | 30.49 | Positive | 31.4 | 30.93 | Positive |
| CDX023 | — | — | Negative | 32.6 | — | Negative |

Example 4

This example illustrates one process for conducting the clinical infectivity test of SARS-CoV-2 to determine the potentially presence of whole virions in the sample using certain embodiments. The steps in the process include:
1. Obtain a clinical sample from a patient. In the case of a respiratory virus such as SARS-CoV-2, a nasopharyngeal swab into saline or other media is commonly used prior to RT-PCR. In the case of blood-borne virus, whole blood may be used. Other biological media may include saliva, urine, cervical or any other bodily fluids associated with the infective agent.

2. Introduce said sample into ATPS system and processing the system according to standard protocols as needed to mix and phase separate.
3. Take aliquot from one of the phases known to be free of RNA that is not contained in a whole intact virus particle.
4. Perform a PCR or other nucleic acid test per protocol.
5. Interpret positive results from said PCR or other nucleic acid test as indicative of the presence of whole intact virus particles in the original sample, thereby indicating potential infectivity status of the patient.

In this example, patients suspected SARS-CoV-2 infection at Cleveland Clinic were screened by nasopharyngeal swab into saline, UTM or VTM, followed by RT-PCR (Roche Diagnostics COBAS 8800) targeting the ORF1 a/b non-structural region and the E envelope region with a limit of detection Ct of about 35. A 400 microliter aliquot of the sample was added into each of two tubes containing An ATPS system comprising dextran-75 (with an average molecular weight of 75,000), Polyethylene glycol PEG-8000 (with an average molecular weight of 8,000), and 0.11 M sodium phosphate buffer (NaPB), pH 7.4 was used. The tubes were sealed, gently mixed by inversion 25× times, and span in a mini-centrifuge for 1 minute until phase separation. Aliquots (350 microliters) from the top phase were added to 100 microliters of PBS and mixed and followed by standard RT-PCR protocol as described above. The results for several patients are shown in the table below:

| Sample ID | PCR Taq Path E | PCR Taq Path ORF 1 | Interpretation |
|---|---|---|---|
| 1 | 22.8 | 23.5 | Infective |
| 2 | 28.3 | 29.8 | Infective |
| 3 | Undetected | Undetected | Non-infective |

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used. Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

When the word "about" is used herein in reference to a number, it should be understood that still another embodiment of the disclosure includes that number not modified by the presence of the word "about."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method, comprising:
    partitioning a biological fluid comprising a virus that causes COVID-19 and free nucleic acid in an aqueous multi-phase partitioning system, wherein at least 95% of the free nucleic acid partitions in a first phase of the partitioning system; and
    determining the virus within the partitioning system.

2. The method of claim 1, comprising determining the virus in a second phase of the partitioning system.

3. The method of claim 1, wherein determining the virus comprises determining the virus within the partitioning system in situ.

4. The method of claim 1, wherein determining the virus comprises removing an aliquot from the partitioning system and determining the virus in the aliquot.

5. The method of claim 1, comprising determining the virus using an agent comprising a signaling moiety and a virus-binding moiety.

6. The method of claim 5, wherein the virus-binding moiety comprises an antibody.

7. The method of claim 5, wherein the signaling moiety comprises gold nanoparticles.

8. The method of claim 7, wherein the gold nanoparticles comprise a virus-binding moiety.

9. The method of claim 1, comprising colorimetrically determining the virus within the partitioning system.

10. The method of claim 1, further comprising releasing nucleic acid from the virus.

11. The method of claim 1, wherein at least 99% of the free nucleic acid partitions in a first phase of the partitioning system.

12. The method of claim 1, wherein the free nucleic acid arises from the virus.

13. The method of claim 1, further comprising determining the free nucleic acid within the partitioning system.

14. The method of claim 13, further comprising determining the free nucleic acid within the first phase of the partitioning system.

15. The method of claim 13, wherein determining the free nucleic acid comprises sequencing the free nucleic acid.

16. The method of claim 15, comprising sequencing the free nucleic acid using PCR.

17. The method of claim 13, wherein determining the free nucleic acid comprises determining a concentration of the free nucleic acid.

18. The method of claim 17, comprising determining a concentration of the free nucleic acid in the first phase of the partitioning system.

19. The method of claim 13, wherein determining the free nucleic acid comprises determining the free nucleic acid within the partitioning system in situ.

20. The method of claim 13, wherein determining the free nucleic acid comprises removing an aliquot from the partitioning system and determining the free nucleic acid in the aliquot.

21. The method of claim 1, wherein the partitioning step occurs in less than 15 minutes.

22. The method of claim 1, wherein the partitioning step occurs in less than 5 minutes.

23. The method of claim 1, wherein the biological fluid arises from a subject suspected of being infected with a virus.

24. The method of claim 1, wherein the biological fluid is blood.

25. The method of claim 1, wherein the biological fluid is saliva.

26. The method of claim 1, wherein the biological fluid is nasal fluid.

27. The method of claim 1, wherein the subject is human.

28. The method of claim 1, wherein the partitioning system consists of two phases.

* * * * *